US009227388B2

(12) United States Patent
Hedberg et al.

(10) Patent No.: US 9,227,388 B2
(45) Date of Patent: Jan. 5, 2016

(54) DEVICES AND METHODS FOR ATTACHING SUPPORT FRAMES TO SUBSTRATES

(71) Applicant: W. L. Gore & Associates, Inc., Newark, DE (US)

(72) Inventors: Brandon C. Hedberg, Flagstaff, AZ (US); William H. Wiley, Flagstaff, AZ (US); Edward E. Shaw, Flagstaff, AZ (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 77 days.

(21) Appl. No.: 13/649,008

(22) Filed: Oct. 10, 2012

(65) Prior Publication Data

US 2013/0306232 A1    Nov. 21, 2013

Related U.S. Application Data

(60) Provisional application No. 61/545,516, filed on Oct. 10, 2011.

(51) Int. Cl.
*B32B 37/00* (2006.01)
*B32B 38/04* (2006.01)
(Continued)

(52) U.S. Cl.
CPC ............... *B32B 38/0004* (2013.01); *A61F 2/07* (2013.01); *A61L 31/022* (2013.01); *A61L 31/10* (2013.01); *B32B 37/185* (2013.01); *A61F 2/856* (2013.01);
(Continued)

(58) Field of Classification Search
CPC ........ B32B 37/00; B32B 38/0004; A61F 2/07; A61F 2/88; A61F 2002/821; A61F 2002/823; A61F 2002/825; A61F 2/856; A61F 2/885; A61F 2/89; A61F 2/91; A61F 2/94; A61F 2/90; Y10T 156/1339; Y10T 156/133
USPC ........... 156/251, 256, 267; 606/198; 623/1.13
See application file for complete search history.

(56) References Cited

U.S. PATENT DOCUMENTS 6,352,561 B1    3/2002    Leopold et al.
6,364,904 B1 *  4/2002    Smith .......................... 623/1.22
(Continued)

FOREIGN PATENT DOCUMENTS

EP    1726271      9/1999
WO    95/26695     10/1995
(Continued)

OTHER PUBLICATIONS

Process For Spot-Welding a Polymer Cover onto a Cardiovascular Stent (RD456093). Research Disclosure, Questel Ireland Ltd; Apr. 2002, p. 1-4.

*Primary Examiner* — Linda L Gray
(74) *Attorney, Agent, or Firm* — Faegre Baker Daniels LLP

(57) ABSTRACT

Devices and methods for attaching support frames to substrates to form articles such as implantable stent grafts can include providing a first laminate material; positioning a support frame onto the first laminate material, the support frame having a pre-formed shape; positioning a second laminate material onto the support frame and first laminate material; bonding the first laminate material to the second laminate material; cutting the first and second laminate materials along opposite sides of the support frame thereby forming a laminated support frame having generally the same pre-formed shape of the support frame; and attaching the laminated support frame to a substrate.

21 Claims, 26 Drawing Sheets

(51) Int. Cl.
- A61F 2/07 (2013.01)
- A61F 2/88 (2006.01)
- B32B 38/00 (2006.01)
- B32B 37/18 (2006.01)
- A61L 31/02 (2006.01)
- A61L 31/10 (2006.01)
- A61F 2/91 (2013.01)
- A61F 2/89 (2013.01)
- A61F 2/856 (2013.01)
- A61F 2/94 (2013.01)
- A61F 2/82 (2013.01)
- A61F 2/90 (2013.01)
- B32B 37/12 (2006.01)
- B32B 38/10 (2006.01)

(52) U.S. Cl.
CPC .... *A61F 2/88* (2013.01); *A61F 2/89* (2013.01); *A61F 2/90* (2013.01); *A61F 2/91* (2013.01); *A61F 2/94* (2013.01); *A61F 2002/075* (2013.01); *A61F 2002/821* (2013.01); *A61F 2002/823* (2013.01); *A61F 2002/825* (2013.01); *A61F 2210/0071* (2013.01); *A61F 2220/005* (2013.01); *A61F 2220/0066* (2013.01); *A61F 2240/001* (2013.01); *B32B 37/00* (2013.01); *B32B 37/12* (2013.01); *B32B 38/10* (2013.01); *B32B 2535/00* (2013.01); *Y10T 156/1052* (2015.01); *Y10T 156/133* (2015.01); *Y10T 156/1339* (2015.01)

(56) References Cited

U.S. PATENT DOCUMENTS

| | | | |
|---|---|---|---|
| 6,551,350 | B1 | 4/2003 | Thornton et al. |
| 6,558,414 | B2 | 5/2003 | Layne |
| 6,770,087 | B2 | 8/2004 | Layne et al. |
| 6,911,040 | B2 | 6/2005 | Johnson et al. |
| 6,981,982 | B2 | 1/2006 | Armstrong et al. |
| 7,004,966 | B2 | 2/2006 | Edwin et al. |
| 7,166,124 | B2 | 1/2007 | Xie et al. |
| 7,238,198 | B2 | 7/2007 | Hartley et al. |
| 7,399,314 | B2 | 7/2008 | Butaric et al. |
| 7,727,271 | B2 | 6/2010 | Kujawski et al. |
| 8,357,194 | B2 | 1/2013 | Majercak |
| 2002/0065550 | A1 | 5/2002 | Smith |
| 2003/0127192 | A1* | 7/2003 | Beaudry ............ 156/352 |
| 2004/0236402 | A1 | 11/2004 | Layne et al. |
| 2004/0247884 | A1* | 12/2004 | Keeney et al. ........ 428/421 |
| 2006/0095114 | A1 | 5/2006 | Hartley et al. |
| 2007/0024465 | A1* | 2/2007 | Howell et al. ........ 340/870.01 |
| 2007/0088425 | A1 | 4/2007 | Schaeffer |
| 2007/0112410 | A1 | 5/2007 | Butaric et al. |
| 2008/0319530 | A1 | 12/2008 | Leewood et al. |
| 2009/0149939 | A1 | 6/2009 | Godlewski et al. |
| 2010/0280590 | A1 | 11/2010 | Sun et al. |

FOREIGN PATENT DOCUMENTS

| WO | 2007/079067 | 7/2007 |
|---|---|---|
| WO | 2008/156683 | 12/2008 |

* cited by examiner

FIG. 21A

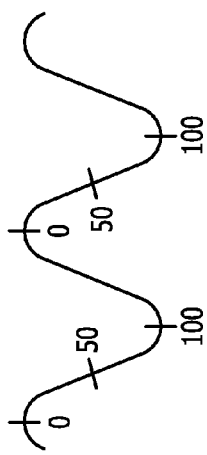

FIG. 21B

| Run | Desc | Strut 1 | Strut 2 | Strut 3 | Strut 4 | Comments |
|---|---|---|---|---|---|---|
| 1 | All mid-struts | 50 | 50 | 50 | 50 | points |
| 2 | All apex tips | 0 | 0 | 0 | 0 | points |
| 3 | Alt apex tips | 0 | | 0 | | points |
| 4 | Alt mid-struts | 50 | | 50 | | points |
| 5 | tips+10% tips | 0,10,90 | 0,10,90 | 0,10,90 | 0,10,90 | points |
| 6 | Alts tips+10% tips | 0,10,90 | | 0,10,90 | | points |
| 7 | 10% tips tips | 10,90 | 10,90 | 10,90 | 10,90 | points |
| 8 | Alt 10% tips only | 10,90 | | 10,90 | | points |
| 9 | 1/4, 3/4 struts | 25,75 | 25,75 | 25,75 | 25,75 | points |
| 10 | Alt 1/4, 3/4 struts | 25,75 | | 25,75 | | points |
| 11 | Evenly spaced thruout | 10,30,50,70,90 | 10,30,50,70,90 | 10,30,50,70,90 | 10,30,50,70,90 | points |
| 12 | The Perko Special | 10,90 | 50 | 10,90 | 50 | points |
| 13 | Tips+mid struts | 0,50 | 0,50 | 0,50 | 0,50 | points |
| 14 | 10% only | 10 | 10 | 10 | 10 | points |
| 15 | Full tip | 0-25 / 75-100 | 0-25 / 75-100 | 0-25 / 75-100 | 0-25 / 75-100 | line |
| 16 | Biased tip only | 0-25 | 75-100 | 0-25 | 75-100 | line |
| 17 | Full tip small | 0-10 / 90-100 | 0-10 / 90-100 | 0-10 / 90-100 | 0-10 / 90-100 | line |
| 18 | Small Biased tip only | 0-10 | 90-100 | 0-10 | 90-100 | line |
| 19 | All | constrain everything | constrain everything | constrain everything | constrain everything | line |
| 20 | All but tips | 0-80 | 20-100 | 0-80 | 20-100 | line |
| 21 | Descending struts only | 0-100 | n/a | 0-100 | n/a | line |
| 22 | Middle 30% | 35-65 | 35-65 | 35-65 | 35-65 | line |
| 23 | Middle 80% | 10-90 | 10-90 | 10-90 | 10-90 | line |

DEVICES AND METHODS FOR ATTACHING SUPPORT FRAMES TO SUBSTRATES

CROSS-REFERENCE TO RELATED APPLICATIONS

This application claims priority to U.S. Provisional Application Ser. No. 61/545,516, entitled "DEVICES AND METHODS FOR ATTACHING SUPPORT FRAMES TO SUBSTRATES" and filed Oct. 10, 2011, which is hereby incorporated by reference in its entirety.

BACKGROUND OF THE INVENTION

1. Field of the Invention

This application relates to devices and methods used to fabricate medical devices. In particular, this application relates to devices and methods used to fabricate endoluminal devices suitable for various medical applications.

2. Background

The functional vessels of human and animal bodies, such as blood vessels and ducts, occasionally weaken. For example, an aortic wall may weaken, resulting in an aneurysm. Upon further exposure to hemodynamic forces, such an aneurysm may rupture, resulting in internal bleeding, and often, death.

The use of an endoluminal device or prosthesis, such as a stent graft is well known in the art as an intervention for repairing weakened, aneurysmal, dissected or ruptured vessels. An endoluminal prosthesis is delivered in a radially compressed configuration using a catheter delivery system. The catheter is introduced into the lumen system and the prosthesis is delivered to the repair site intraluminally. The prosthesis is then expanded to engage the luminal wall. The prosthesis provides some or all of the functionality of the original, healthy vessel and/or preserves any remaining vascular integrity by replacing a length of the existing vessel wall that contains the site of vessel weakness or failure. Endoluminal prostheses such as stent grafts may be used for the treatment of various functional vessels, including body lumens such as the esophagus, bile duct, or blood vessels.

Presently, the manufacture of stent grafts or covered stents requires specialized secondary procedures or specialized stent-attachment mechanisms. For example, the stent may be attached to a graft using external components such as hooks, sutures, adhesives and adhesive film wrappings. Such components and processes are both labor-intensive and costly.

Thus, there is a need for an endoluminal prosthesis that includes a stent and a graft where the stent and graft are secured together without the use of labor-intensive and costly attachment procedures or mechanisms.

BRIEF DESCRIPTION OF THE DRAWINGS

The accompanying drawings are included to provide a further understanding of the invention and are incorporated in and constitute a part of this specification, illustrate embodiments of the invention and together with the description serve to explain the principles of the invention.

FIG. 21A is a schematic of an undulating support frame defining specific locations along the support frame;

FIG. 21B is a table defining 23 different patterns of support frame to substrate attachment points;

DETAILED DESCRIPTION OF THE ILLUSTRATED EMBODIMENTS

Figure 1:
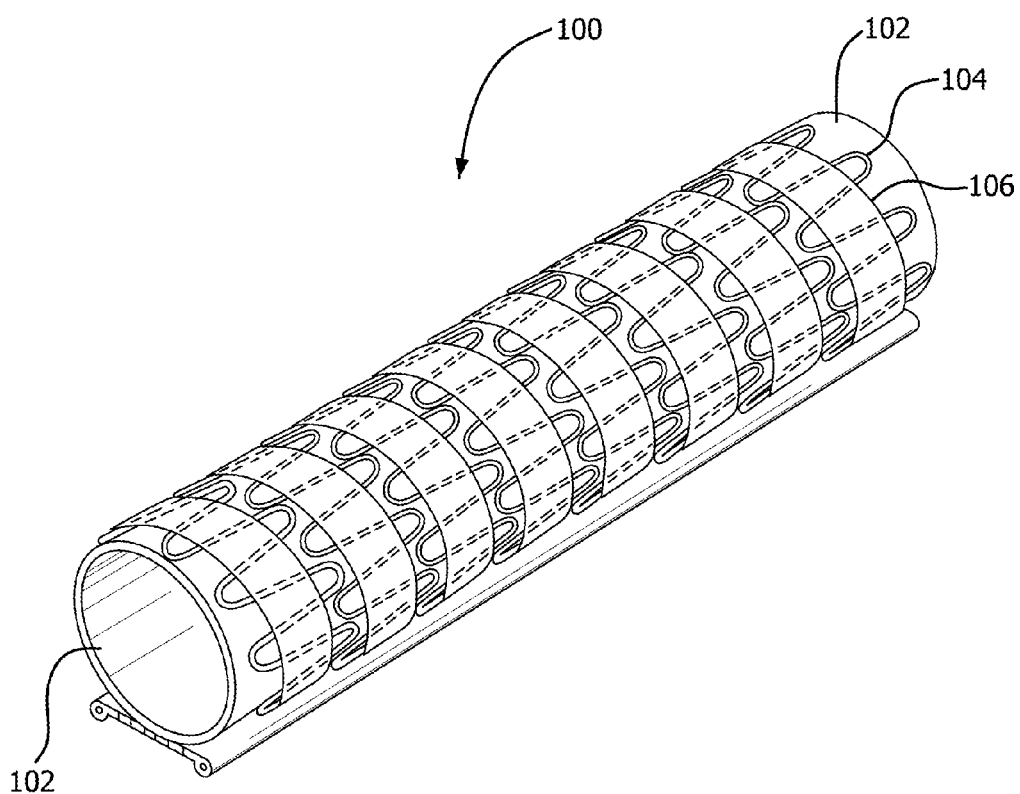
FIG. 1 is a perspective view of a stent graft having a support frame attached to a substrate.

Shown in FIG. 1 is a perspective view of a typical stent graft 100 configuration having a tubular graft 102, a support frame or stent 104 and a support frame to graft attachment film 106. The support frame 104 as shown is a wire formed to have an undulating helical shape. The undulating shape comprises a series of apices that form a series of peaks and valleys. Such undulating helical supports can be self-expanding or can be mechanically expanded by a balloon or other expansion device. Undulating supports may also be in the form of separate rings vs. a continuous helix. To enhance the flexibility of the stent graft 100, the graft attachment film 106 covers and joins the support frame to the graft on only a portion of the support frame undulating shape. As shown, the graft attachment film does not cover the support frame apices. Stents, as generally depicted in FIG. 1, can be fabricated according to the methods and materials as generally disclosed in, for example, U.S. Pat. No. 6,042,605 issued to Martin, et al., U.S. Pat. No. 6,361,637 issued to Martin, et al. and U.S. Pat. No. 6,520,986 issued to Martin, et al.

A support frame can be any structure used to provide rigidity to a device. For example a support frame can be incorporated into a stent, a filter, a closure device, an occlusion device, a valve, an embolectomy device, a valveulatom device, a side branch to main body joining device, an introducer, a guide catheter or other device. Support frames can be fabricated from a variety of bio-compatible materials including commonly known materials (or combinations of materials) used in the manufacture of implantable medical devices. Typical materials include 316L stainless steel, cobalt-chromium-nickel-molybdenum-iron alloy ("cobalt-chromium"), other cobalt alloys such as L605, tantalum, Nitinol, or other bio-compatible metals. Sputtered or electroplated thin metallic films can also be used as a support frame.

A support frame can have any cross-sectional profile. For example a support frame can have a cross-sectional profile that is essentially circular, oval, square, rectangular, regular polygon or non-regular polygon. The cross-sectional profile can also vary along the length of the support frame. For example a support frame can have a circular profile along one section and a rectangular profile along another section.

A graft can be defined as an implantable, generally tubular device that enables a stent to be essentially impervious to blood or serum flow. A graft can comprise any bio-compatible polymer and can be extruded, coated or formed from wrapped films. Typical polymers used to form grafts may include nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, and elastomeric organosilicon polymers. Suitable biodegradable materials can be used for specific applications. Sputtered or electroplated thin metallic films can also be used as a graft material.

The present invention comprises a variety of devices and methods used to attach a support frame to a graft.

One general group of devices and methods of the present invention include the use of a support frame anchor. Various forms of anchors can be used to attach a support frame to a graft.

Figure 2:
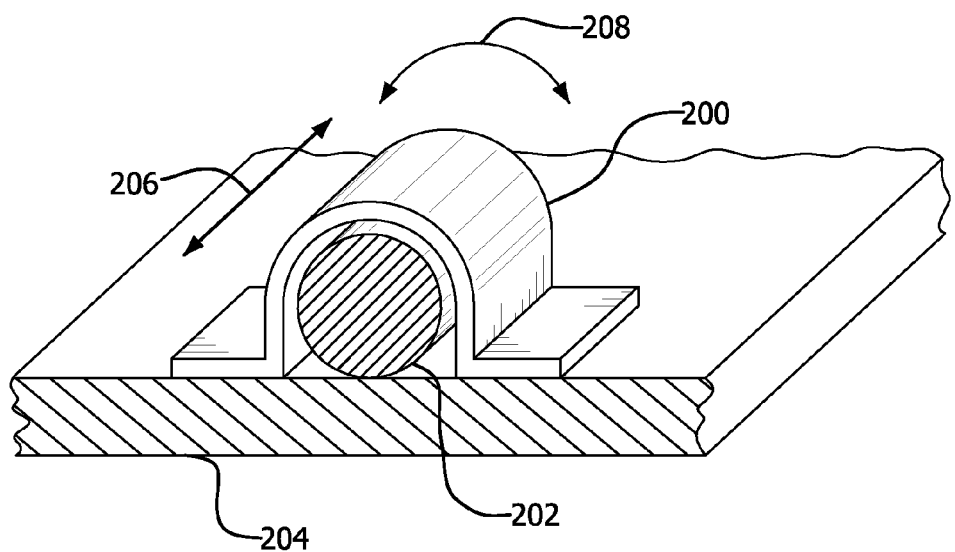
FIG. 2 is a partial perspective view of an anchor used to attach a support frame to an substrate.

Shown in FIG. 2 is a anchor 200 surrounding a support frame 202 having a generally circular cross-section. The anchor 200 is used to attach the support frame 202 to an underlying substrate 204. The substrate 204 can be configured as a graft. The anchor 200 can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PE-BAX) and metals such as stainless steel and nickel/titanium alloys. Sputtered or electroplated thin metallic films may also be incorporated into an anchor.

The anchor 200 can be extruded, molded or formed in place over the support frame, such that the support frame is attached to the underlying substrate. In one process, the anchor can be automatically picked and placed onto the support frame. Various means can be used to precisely locate the support frame and corresponding attachment location. For example the precise wire location can be determined by visual, thermal, Hall effect, electrical charge, electrical current flow, or other feedback that would provide the presence and location of the support frame.

The anchor 200 can be attached to the support frame 202 and/or to the substrate 204 by thermally, ultrasonically or pressure reflowing a thermal-plastic anchor onto the wire and/or the substrate. Electrical current, RF energy, inductance, or other means may be used to warm or otherwise heat the wire to cause the anchor material to reflow. Adhesives and thermo-set plastics may also be incorporated to form or enhance the attachment. The adhesives may be cured or set by conventional means including RF, Ultraviolet, chemical, heat or pressure activation. If desired the anchor may be attached only to the substrate, allowing relative translation between the anchor and the support frame along a longitudinal direction or rotational direction, as depicted by direction arrows 206 and 208.

Figure 3:
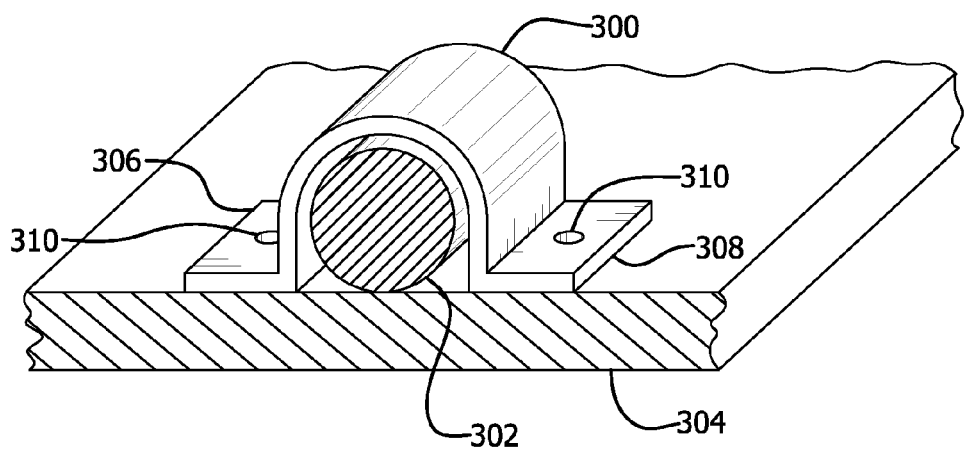
FIG. 3 is a partial perspective view of an anchor used to attach a support frame to a substrate, the anchor having through holes to enhance the bonding to the substrate.

Shown in FIG. 3 is an anchor 300 surrounding a support frame 302 having a generally circular cross-section. The anchor 300 is used to attach the support frame 302 to an underlying substrate 304. Anchor legs 306, 308 can incorporate holes or perforations 310 that can be used to affect or enhance the attachment of the anchor 300 to the substrate 304. For example a thermal-plastic, adhesive or thermal-set material may be applied into the holes 310 to attach the anchor to the substrate.

Figure 4:
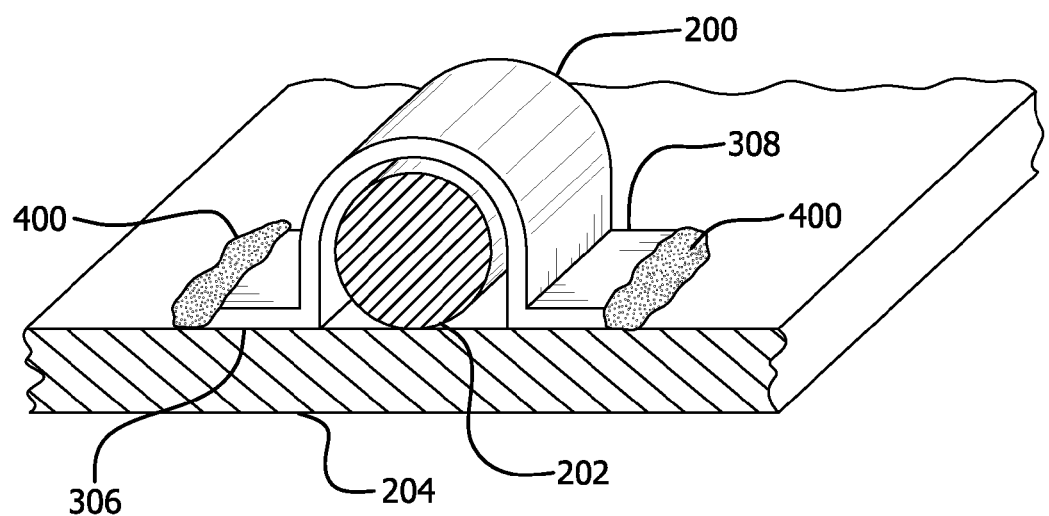
FIG. 4 is a partial perspective view of an anchor used to attach a support frame to a substrate, the anchor having an additional adhesive to enhance the bonding to the substrate.

Shown in FIG. 4 is an anchor 200 surrounding a support frame 202 having a generally circular cross-section. The anchor 200 is used to attach the support frame 202 to an substrate 204. The anchor legs 306, 308 are shown attached to the substrate 204 by the use of a thermal-plastic, adhesive or thermal-set material 400.

Figure 5:
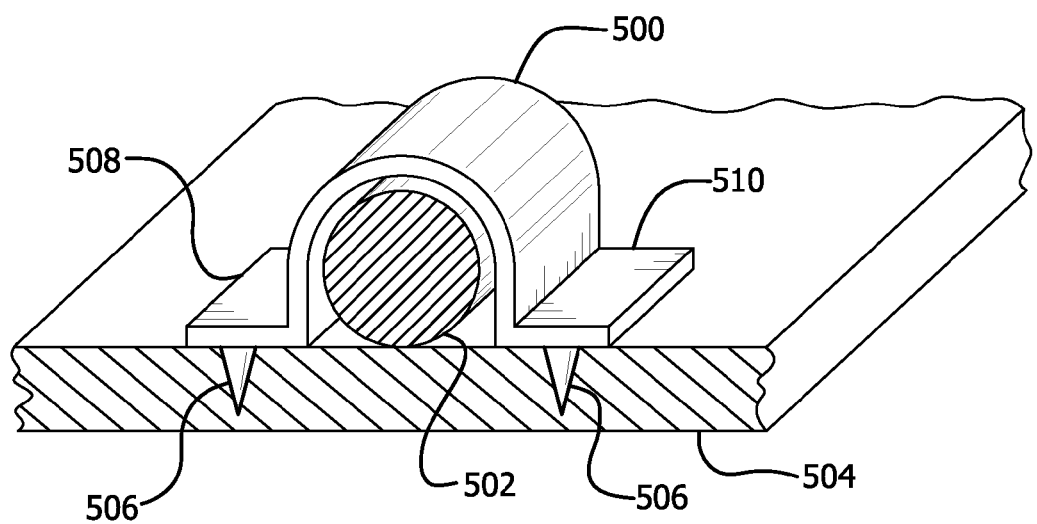
FIG. 5 is a partial perspective view of an anchor used to attach a support frame to a substrate, the anchor having piercing spikes to enhance the bonding to the substrate.

Shown in FIG. 5 is an anchor 500 surrounding a support frame 502 having a generally circular cross-section. The anchor 500 is used to attach the support frame 502 to an underlying substrate 504. Incorporated into the anchor legs 508, 510 are perforating features 506. The perforation features 506 can be used to puncture the substrate 504 and therefore provide a more robust attachment of the anchor 500 to the substrate 504. A thermal-plastic, adhesive or thermal-set material can be incorporated onto the perforation features 506 to enhance the anchor to substrate attachment.

Figure 6A:
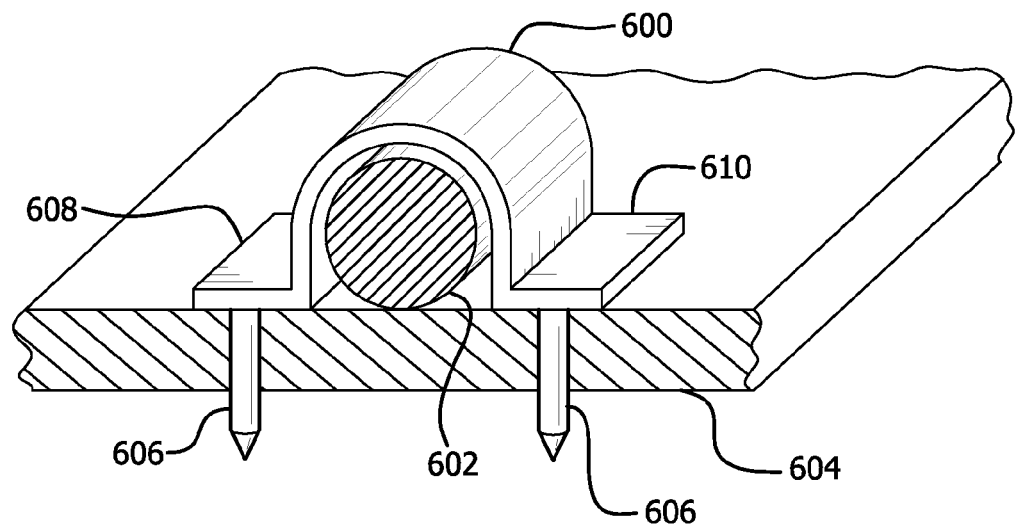
FIG. 6A is a partial perspective view of an anchor used to attach a support frame to a substrate, the anchor having extended piercing spikes to enhance the bonding to the substrate.
Figure 6B:
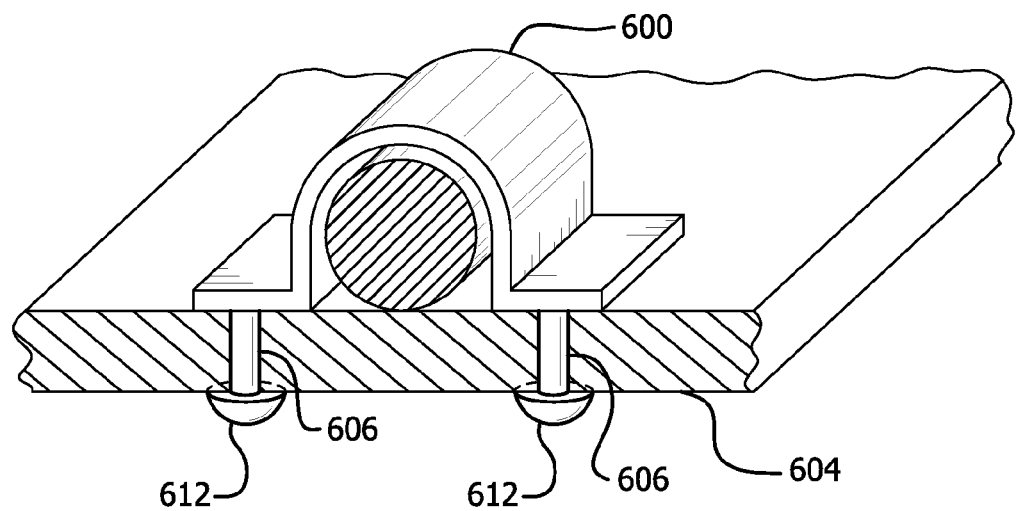
FIG. 6B is a partial perspective view of an anchor used to attach a support frame to a substrate, the anchor having extended piercing spikes that have been formed into rivet heads.

FIGS. 6A and 6B are anchors similar to that shown in the previous FIG. 5. Shown in FIG. 6A is anchor 600 having two legs 608, 610. The anchor is shown surrounding a support frame 602. Protruding from the legs 608, 610 are long perforation spikes 606. When placed into the substrate 604 the spikes 606 extend through the substrate 604. As shown in FIG. 6B, fixation features 612 can the be added to the extending spikes 606. Fixation features 612 can be formed by reflowing the extending spikes by conventional means, or by affixing additional components to the extending spikes.

Figure 7A:
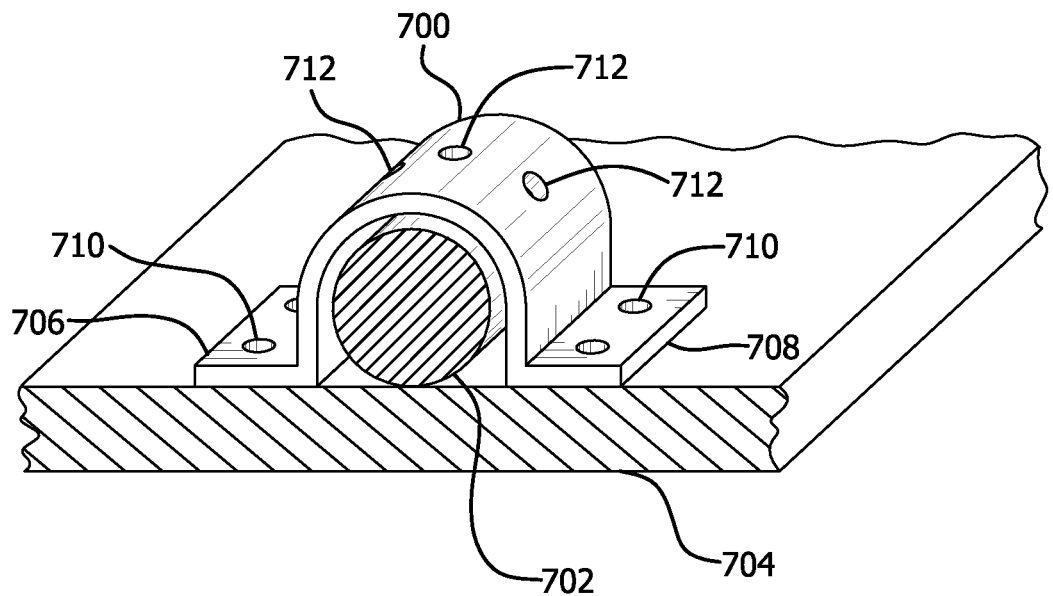
FIG. 7A is a partial perspective view of an anchor used to attach a support frame to a substrate, the anchor having through holes to enhance the bonding to the substrate and the bonding to the support frame.
Figure 7B:
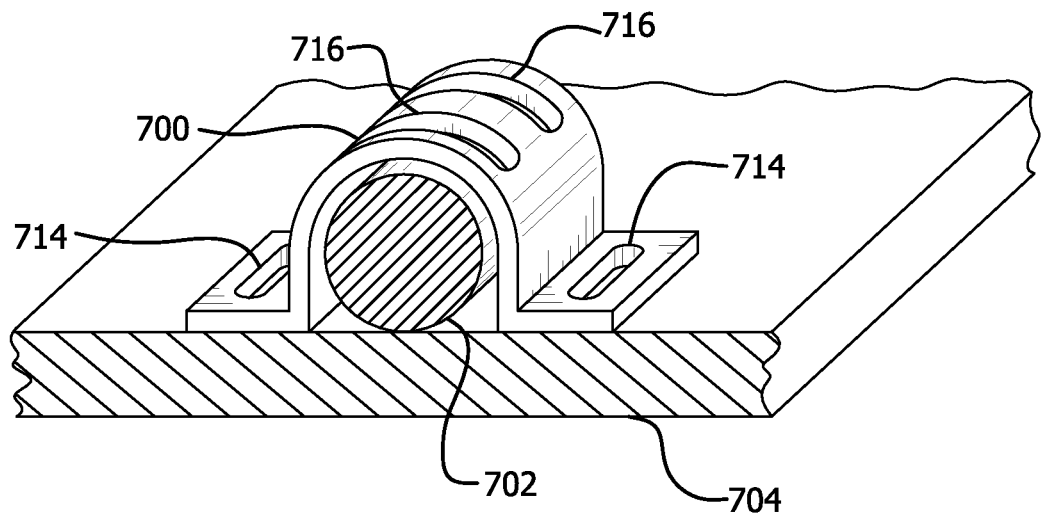
FIG. 7B is a partial perspective view of an anchor used to attach a support frame to a substrate, the anchor having elongated through holes or slots to enhance the bonding to the substrate and the bonding to the support frame.

FIGS. 7A and 7B are anchors similar to that shown in the previous FIG. 3. Shown in FIG. 7A is an anchor 700 surrounding a support frame 702 having a generally circular cross-section. The anchor 700 is used to attach the support frame 702 to an underlying substrate 704. Anchor legs 706, 708 can incorporate single or multiple holes or perforations 710 that can be used to affect or enhance the attachment of the anchor 700 to the substrate 704. For example a thermal-plastic, adhesive or thermal-set material may be applied into the holes 710 to attach the anchor to the substrate. Additionally, single or multiple holes or perforations 712 may be added to the anchor portion that surrounds the support frame. These holes or perforations can be used to affect or enhance the attachment of the anchor 700 to the support frame 702. For example a thermal-plastic, adhesive or thermal-set material may be applied into the holes 712 to attach the anchor to the support frame.

In a similar fashion, single or multiple elongated slots or other non-circular holes may be added to the anchor. Shown in FIG. 7B is an anchor 700 having elongated slots 714, 716 incorporated into the anchor legs and/or into the anchor portion that surrounds the support frame. The elongated slots or other non-circular holes can be used to affect or enhance the attachment of the anchor 700 to the support frame 702 and/or to the substrate 704.

Figure 8:
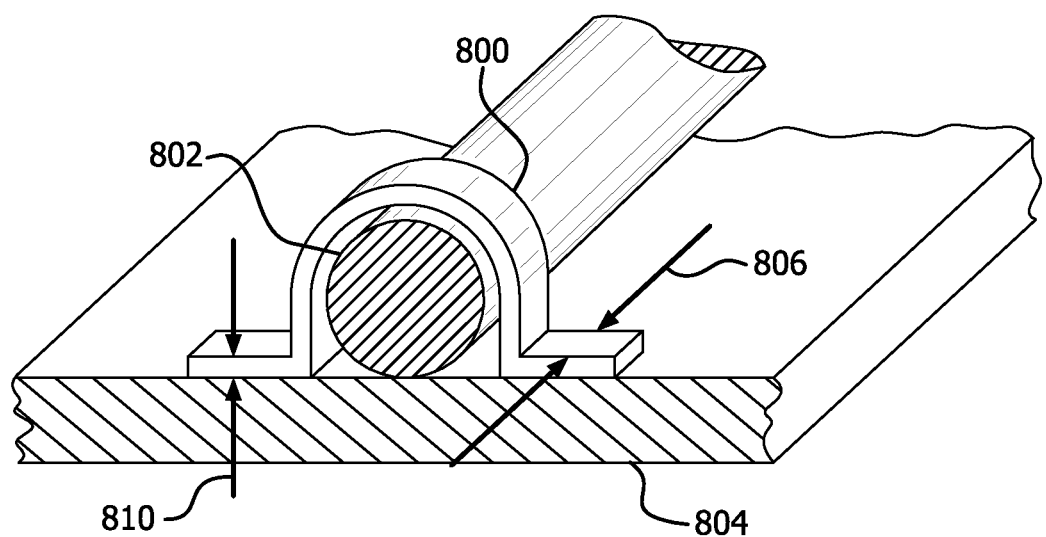
FIG. 8 is a partial perspective view of an anchor used to attach a support frame to a substrate, the anchor having variable widths and thicknesses.

Shown in FIG. 8 is an anchor 800 surrounding a support frame 802 having a generally circular cross-section. The anchor 800 is used to attach the support frame 802 to an underlying substrate 804. The anchor 800 can be tailored to have any desired length 806, depending on the anchor material and intended use. For example anchors can have a length ranging from about 0.0005" to about 1.0" or more. Anchor 800 can have a thickness 810 ranging from about 0.0001" to about 0.04" or more.

Another general group of devices and methods of the present invention include various staples used to attach a support frame to a substrate. Various forms of staples can be used to attach a support frame to a substrate.

Figure 9A:
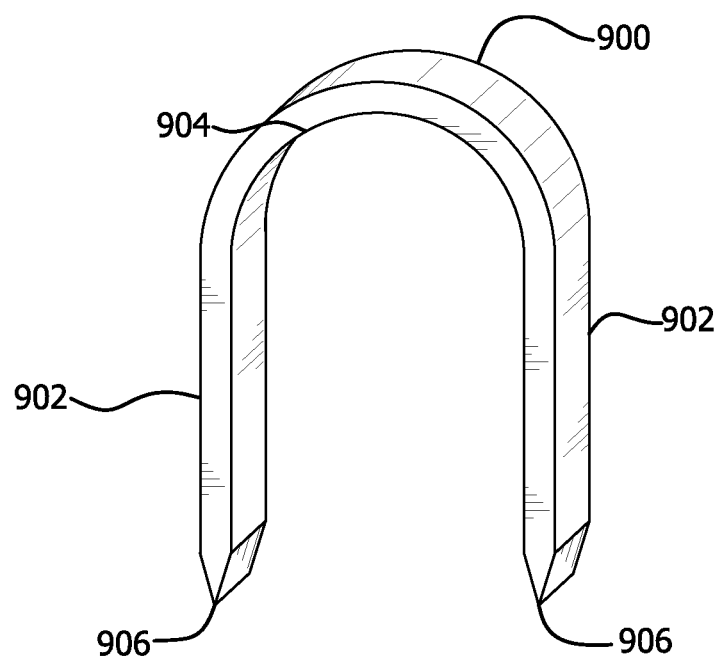
FIG. 9A is a perspective view of a staple used to attach a support frame to a substrate.
Figure 9B:
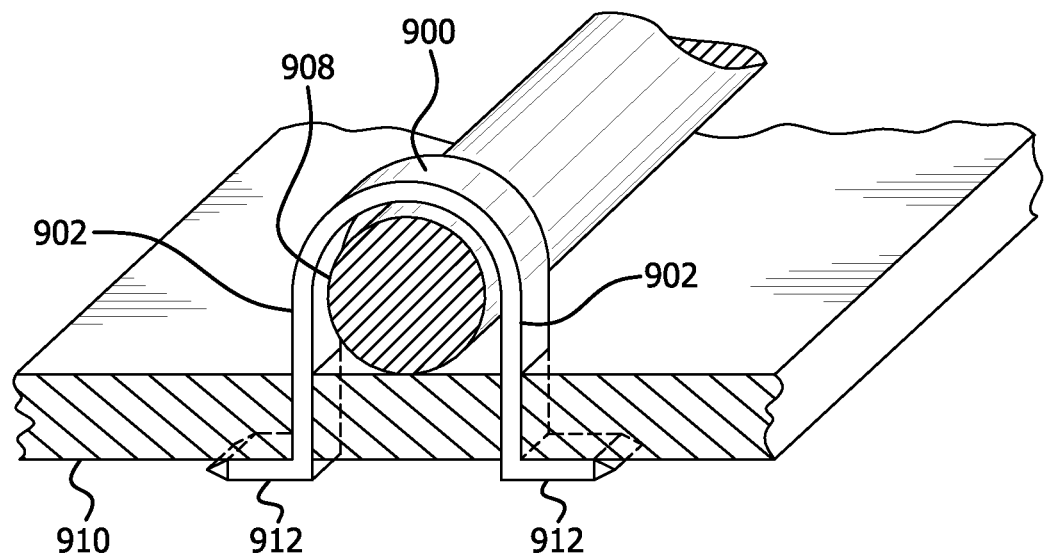
FIG. 9B is a perspective view of a staple used to attach a support frame to a substrate, the staple being deformed below the substrate.

Shown in FIG. 9A is a staple 900 having opposed legs 902 joined to an anchoring portion 904. The opposed legs 902 may optionally have piercing points 906 to assist in the puncturing of a substrate. Shown in FIG. 9B is a staple 900 partially surrounding a support frame 908. The staple opposing legs 902 are shown protruding through a substrate 910. The ends 912 of the staple opposing legs 902 are shown deformed about the substrate 910, resulting in a support frame 908 join to the substrate 910.

Figure 10A:
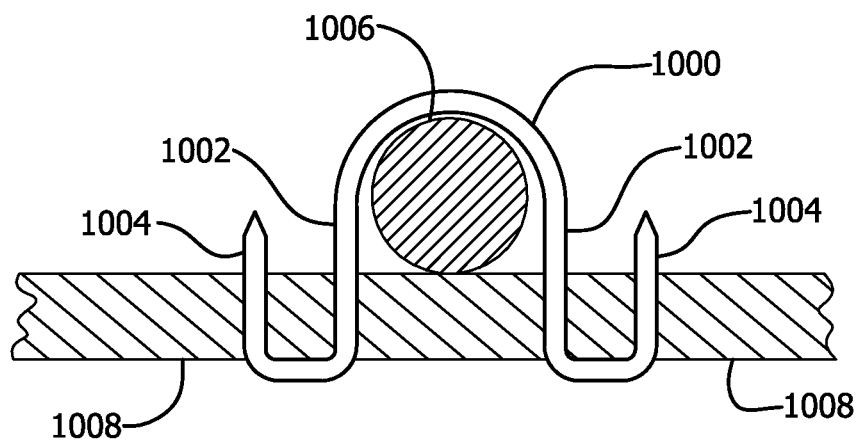
FIG. 10A is a front cross-sectional view of a staple used to attach a support frame to a substrate, the staple being deformed about two planes.
Figure 10B:
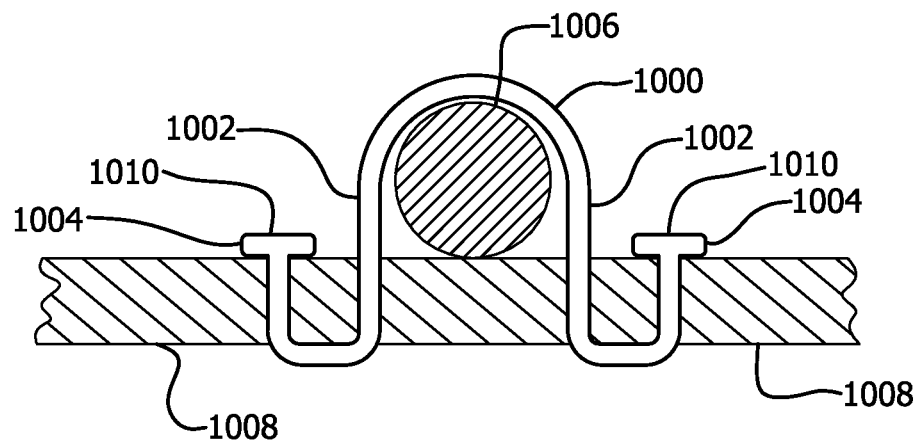
FIG. 10B is a front cross-sectional view of a staple used to attach a support frame to a substrate, the staple ends being deformed into rivet heads.
Figure 10C:
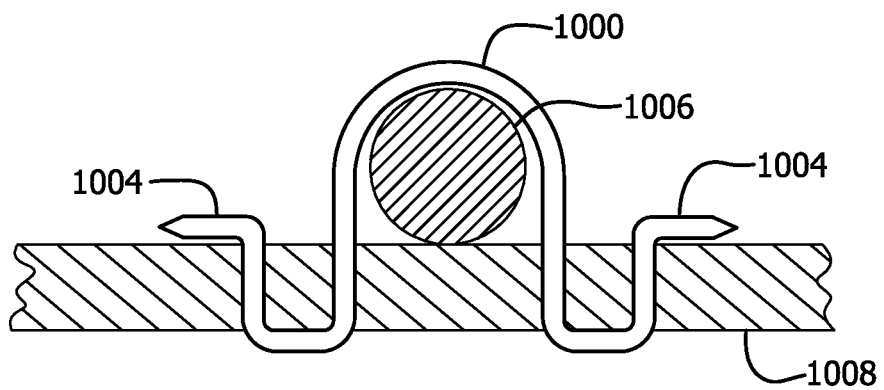
FIG. 10C is a front cross-sectional view of a staple used to attach a support frame to a substrate, the staple being deformed about three planes.

FIGS. 10A and B show an alternate configuration, similar to that shown in FIG. 9. As shown in FIG. 10A a staple 1000 partially surrounds a support frame 1006. The staple opposed legs 1002 are shown protruding through a substrate 1008. The ends 1004 of the opposing staple legs 1002 are shown piercing through the substrate 1008. The opposing staple legs 1002 are shown re-piercing the substrate, forming a double pierced, support frame 1006 join to the substrate 1008. FIG. 10B shows a similar staple 1000 wherein the opposing leg ends 1004 are deformed to form a head 1010. FIG. 10C shows a similar staple 1000 wherein the opposing leg ends 1004 are deformed and folded over onto the substrate 1008, resulting in a support frame 1006 join to the substrate 1008.

Figure 11A:
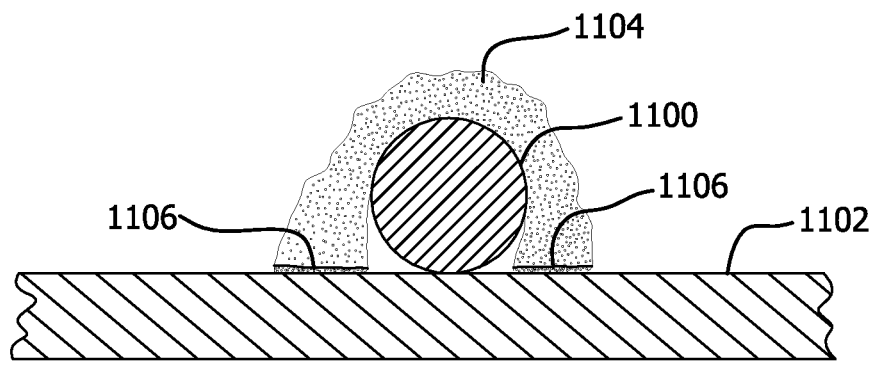
FIG. 11A is a front cross-sectional view of a support frame attached to a substrate by an over-flowed adhesive.

FIGS. 11A and B show an alternate configuration of attaching a support frame to a substrate. Shown in FIG. 11A is a cross-sectional view of a support frame 1100 positioned onto a substrate 1102. An adhesive 1104 is shown partially encapsulating the support frame. The adhesive therefore is used to form a join 1106 between the support frame 1100 and the substrate 1102. The adhesive 1104 can comprise a thermoplastic that is heated and reflowed onto the support frame 1100 and substrate 1102. The adhesive 1104 can be applied by automated "hot-melt" dispensers or other commonly known means.

Figure 11B:
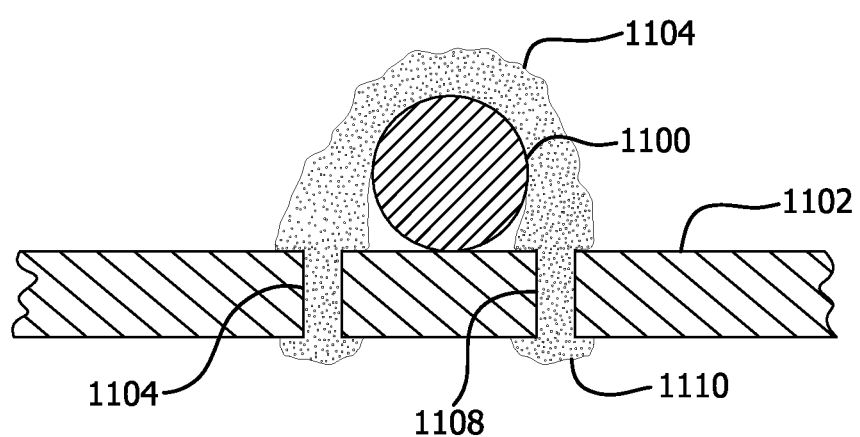
FIG. 11B is a front cross-sectional view of a support frame attached to a substrate by a reflowed adhesive, wherein the adhesive has reflowed into substrate anchoring holes.

The adhesive 1104 can, in an alternate embodiment, penetrate the substrate 1102, as shown in FIG. 11B. Shown in FIG. 11B is a support frame 1100 positioned onto a substrate 1102. An adhesive 1104 is shown partially encapsulating the support frame. The adhesive 1104 is further shown reflowed into holes 1108 in the substrate 1102. The protruding ends of the thermoplastic can be optionally formed into "rivet heads" 1110.

As the term "elastomer" is used herein it defines a polymer that has the ability to be stretched to at least twice its original length and to retract rapidly to approximately its original length when released. The term "elastomeric" is intended to describe a condition whereby a polymer displays stretch and recovery properties similar to an elastomer, although not necessarily to the same degree of stretch and/or recovery.

As the term "thermoplastic" is used herein it defines a polymer that softens when exposed to heat and returns to its original condition when cooled to room temperature. Such a polymer can be made to soften, flow or take on new shapes, without significant degradation or alteration of the polymer's original condition, by the application of heat or heat and pressure.

In contrast to a thermoplastic polymer, a "thermoset" polymer is hereby defined as a polymer that solidifies or "sets" irreversibly when cured. A determination of whether a polymer is a "thermoplastic" polymer within the meaning of the present invention can be made by slowly elevating the temperature of a stressed specimen and watching for deformation.

If the polymer can be made to soften, flow, or take on a new shape, without significant degradation or alteration of the polymers original chemical condition, then the polymer is considered to be a thermoplastic. If only small amounts of material are available it may be necessary to use a hot stage microscope for this determination.

In addition to the polymeric materials previously listed, other suitable polymers include thermoplastic elastomers (e.g., a heat shrinkable polymers). Examples of such polymers include polyamides (e.g., nylons), copolymers of polyamides (e.g., nylon-polyether copolymers), polyesters (e.g., polyethylene terephthalate (PET) polymers, polybutylene terephthalate (PBT) polymers), copolymers of polyesters, polyetheretherketones (PEEKs), polyurethanes, polyethylenes, polypropylenes, copolymers and ionomers of ethylene, copolymers and ionomers of polypropylene, polystyrenes and copolymers of polystyrenes. Examples of commercially available polyesters include the Selar PT family of polymers (e.g., Selar PT 8307, Selar PT4274, Selar PTX280), which are commercially available from E. I. DuPont de Nemours (Wilmington, Del.), the Cleartuf family of polymers (e.g., Cleartuf 8006), which are commercially available from M&G Polymers (Apple Grove, W.V.), the Traytuf family of polymers (e.g., Traytuf 1006), which are commercially available from the Shell Chemical (Houston, Tex.), the Melinar family of polymers, commercially available from E. I. DuPont de Nemours (Wilmington, Del.), the Celanex family of polymers, commercially available from Ticona (Summit, N.J.), the Riteflex family of polymers, commercially available from Ticona (Summit, N.J.), the Hytrel family of polymers (e.g., Hytrel 5556, Hytrel 7246, Hytrel 4056), commercially available from E. I. DuPont de Nemours (Wilmington, Del.), the Arnitel family of polymers (e.g., Arnitel EM630), commercially available from DSM (Erionspilla, Ind.). Examples of commercially available polyamides include Nylon 12, commercially available from Atofina (Philadelphia, Pa.), Nylon 6, commercially available from Honeywell (Morristown, N.J.), Nylon 6/10, commercially available from BASF (Mount Olive, N.J.), Nylon 6/12, commercially available from Ashley Polymers (Cranford, N.J.), Nylon 11, Nylon MXD-6, and the Grivory family of polymers, commercially available from EMS (Sumter, S.C.), the Grilamid® family of polymers (e.g., Grilamid L25, Grilamid L20), commercially available from EMS (Sumter, S.C.), the Vestamid family of polymers (e.g., Vestamid L2101F), commercially available from Daicel-Degussa Ltd., and the PEBAX® family of polymers (e.g., PEBAX 5533, PEBAX 2533, PEBAX 7033), commercially available from Atofina (Philadelphia, Pa.), the Trogamid family of polyamides from Daicel-Degussa, Cristamid MS1100 from Atofina (Philadelphia, Pa.), and Vestamid L2101F nylon 12 from Degussa AG. An example of a commercially available polyethylene is Marlex 4903 high density polyethylene from Phillips 66 (Bartlesville, Okla.).

Alternately, a thermoset material can be used as the adhesive 1104, as shown in FIGS. 11A and 11B.

Figure 12A:
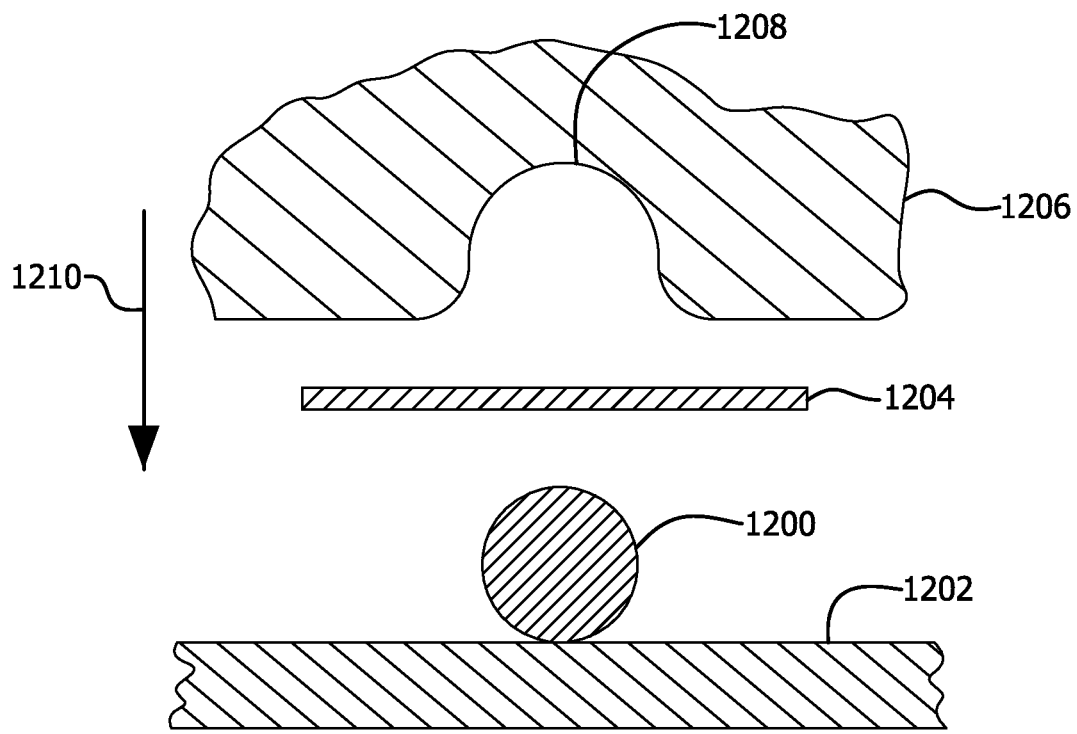
FIG. 12A is a front cross-sectional view of a support frame, a substrate, a thermoplastic ribbon and a forming die.
Figure 12B:
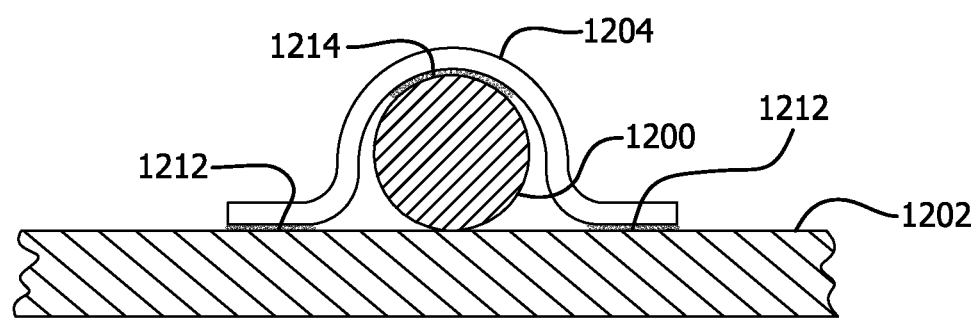
FIG. 12B is a front cross-sectional view of a support frame, a substrate, a thermoplastic ribbon and a forming die, showing the ribbon deformed onto the support frame and the substrate.

FIGS. 12A and 12B show an alternate configuration of attaching a support frame to a substrate. Shown in FIG. 12A is a cross-sectional view of a support frame 1200 positioned onto a substrate 1202. Positioned above the support frame 1200 is a thermoplastic ribbon or strip 1204. A heated forming die 1206 is shown positioned above the thermoplastic ribbon 1204. The forming die 1206 has a die cavity 1208 configured according to the dimensions and profiles of the support frame 1200 and thermoplastic ribbon 1204. When the heated die is lowered (as indicated by direction arrow 1210), the die cavity 1208 engages the thermoplastic ribbon 1204 and deforms the ribbon onto the support frame 1200. As shown in FIG. 12B, the thermoplastic ribbon 1204 has been heated and reflowed around the support frame 1200, forming an anchor similar to those previously described. The thermoplastic ribbon 1204 has also reflowed onto the substrate 1202. By the application of sufficient heat and pressure, bonds 1212 are formed between the support frame 1200 and the substrate 1202. An additional bond 1214 can similarly be formed between the thermoplastic ribbon 1204 and the support frame 1200.

An automated process can be used to locate a target position on a support frame, index and align a thermoplastic ribbon to the target position and then heat and compress and reflow the thermoplastic ribbon onto the support frame and underlying substrate. Visual, thermal, Hall effect, magnetic or other means may be used to determine the locations of various target positions. Individual components (forming die 1206, thermoplastic ribbon 1204, support frame 1200 and substrate 1202) can be heated by electrical resistance, inductive heating, RF heating, microwaves, infrared sources, lasers, hot gasses, flames or other commonly known methods. The relative positions of the individual components can be pre-aligned or aligned during the automated process.

Figure 13A:
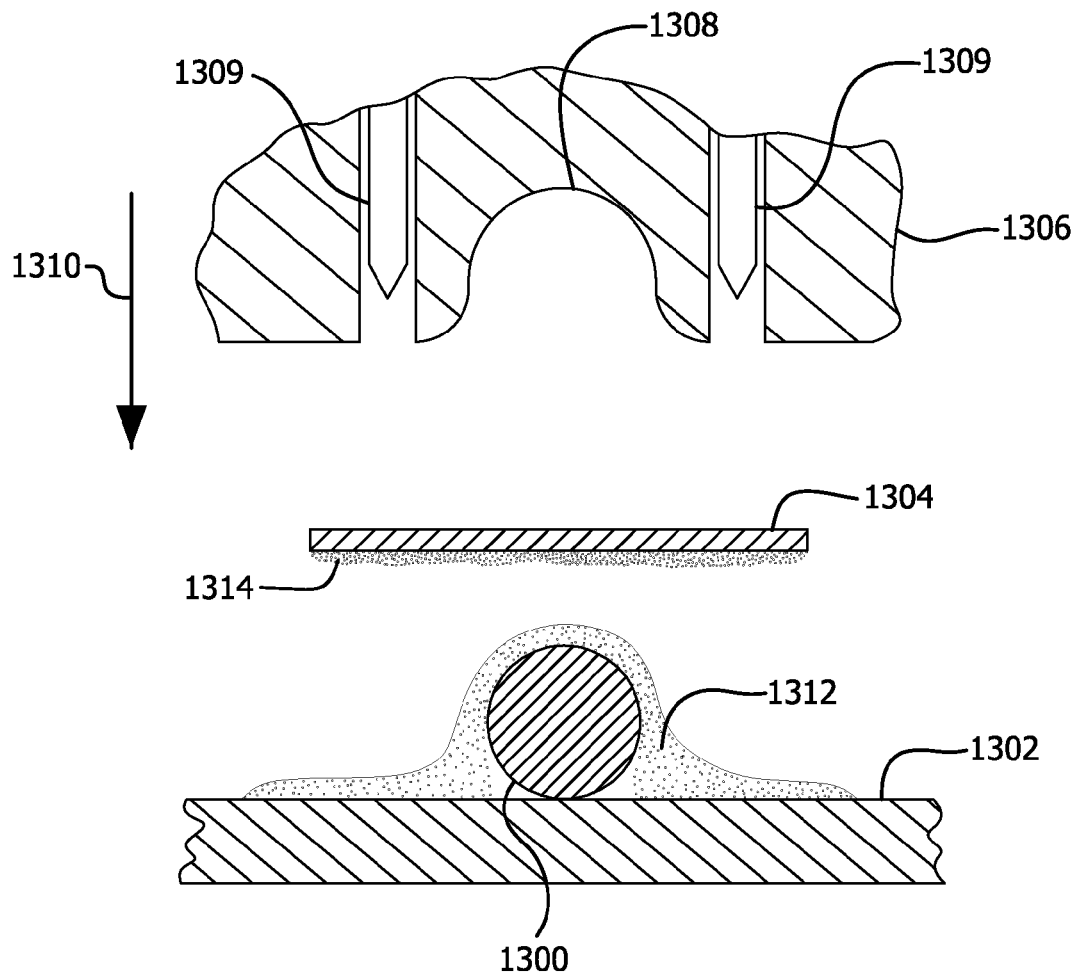
FIG. 13A is a front cross-sectional view of a support frame, a substrate, a thermoplastic ribbon, an additional adhesive and a forming die with perforating pins.
Figure 13B:
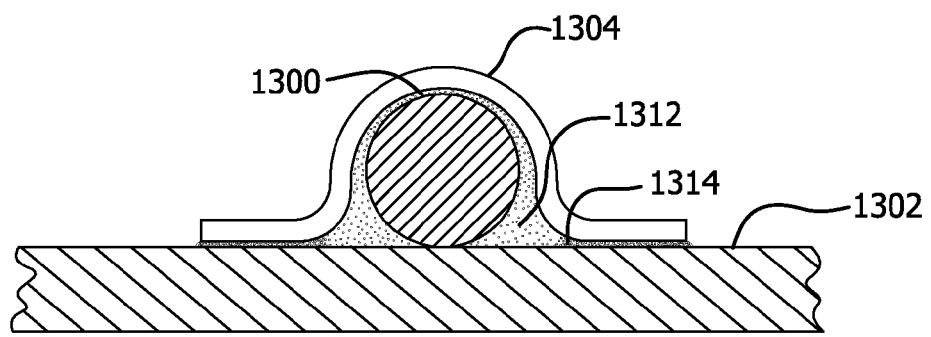
FIG. 13B is a front cross-sectional view of a support frame, a substrate, a thermoplastic ribbon, a forming die, and an additional adhesive, showing the ribbon deformed onto the support frame and the substrate.
Figure 13C:
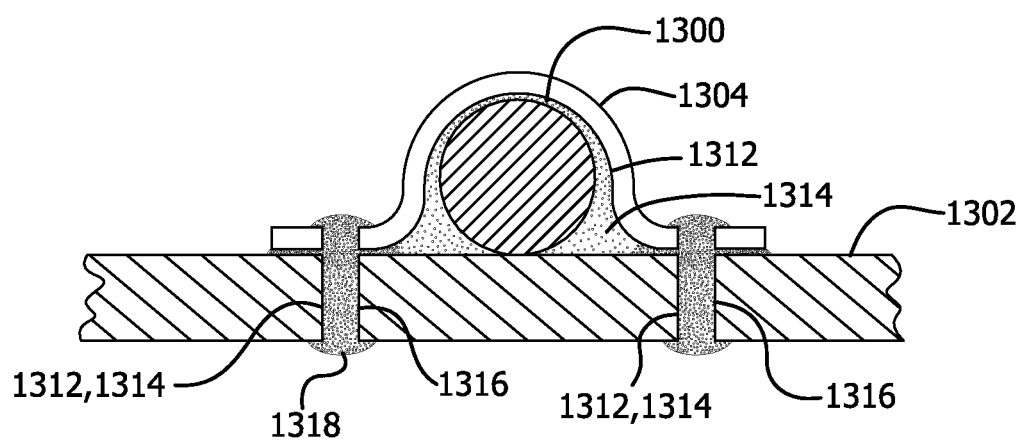
FIG. 13C is a front cross-sectional view of a support frame, a substrate, a thermoplastic ribbon, and an additional adhesive, wherein an adhesive has reflowed into holes perforated through the substrate.

An alternate process for attaching a support frame to a substrate is shown in FIGS. 13A through 13C. Shown in FIG. 13A is a cross-sectional view of a support frame 1300 positioned onto a substrate 1302. Positioned above the support frame 1300 is a thermoplastic ribbon or strip 1304. A heated forming die 1606 is shown positioned above the thermoplastic ribbon 1304. The forming die 1306 has a die cavity 1308 configured according to the dimensions and profiles of the support frame 1300 and thermoplastic ribbon 1304. When the heated die is lowered (as indicated by direction arrow 1310), the die cavity 1308 engages the thermoplastic ribbon 1304 and deforms the ribbon onto the support frame 1300.

Additional bonding materials 1312 and 1314 can be applied to the support frame 1300, to the substrate 1302 and/or to the thermoplastic ribbon 1304. These additional bonding materials can comprise a thermoplastic, an adhesive, a thermal-set or cross-linkable material. As shown in FIG. 13B, the thermoplastic ribbon 1304 has been heated and reflowed around the support frame 1300, forming an anchor similar to those previously described. The thermoplastic ribbon 1304 has also reflowed onto the substrate 1302. The additional bonding materials 1312 and 1314 can be used to enhance the bond strength between the individual components.

Additional materials can be applied in a process similar to that used to apply the additional bonding materials 1312 and 1314. These additional materials can be used as radiopaque markers, therapeutic agents or as bonding inhibitors that would allow relative sliding or rotational movement between the support frame 1300 and the substrate 1302.

The forming die 1306 may also include a means (FIG. 13A, 1309) to perforate the substrate 1302 and/or thermoplastic ribbon 1304. As the forming die 1306 compresses onto the substrate 1302, the perforating pins 1309 can be extended out of the forming die 1306 and form holes or perforations in the substrate 1302 and/or the thermoplastic ribbon 1304. As shown in FIG. 13C, a substrate 1302 has perforations 1316 filled by the additional bonding materials 1312 and 1314. The bonding material extending out of the perforations 1316 can be optionally formed into a securing or rivet head 1318.

Figure 14A:
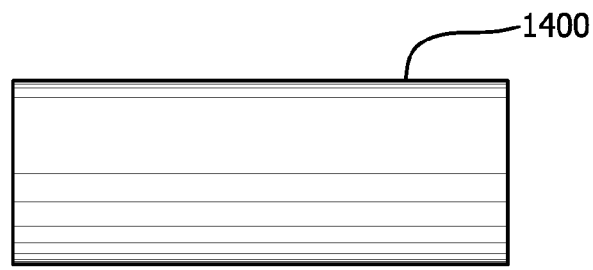
FIG. 14A is a front view of a tubular substrate.

An ablative or removal process is described in FIGS. 14A through 14D. Shown in FIG. 14A is a tubular graft 1400. Potential materials for a substrate or graft member 1400 include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. One preferred embodiment for a substrate material is ePTFE. The substrate and/or graft member may include a bioactive agent.

Figure 14B:
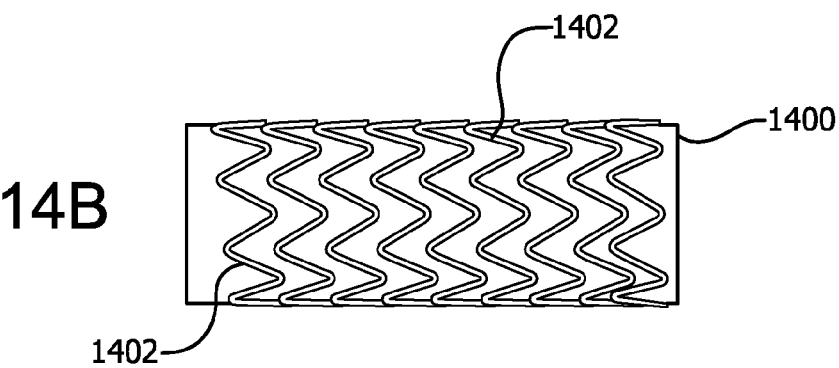
FIG. 14B is a front view of a support frame placed over a tubular substrate.

FIG. 14B depicts a support frame 1402 positioned onto the substrate or graft member 1400. Stents can have various configurations as known in the art and can be fabricated, for example, from cut tubes, wound wires (or ribbons) or flat patterned sheets rolled into a tubular form. Stents can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

Figure 14C:
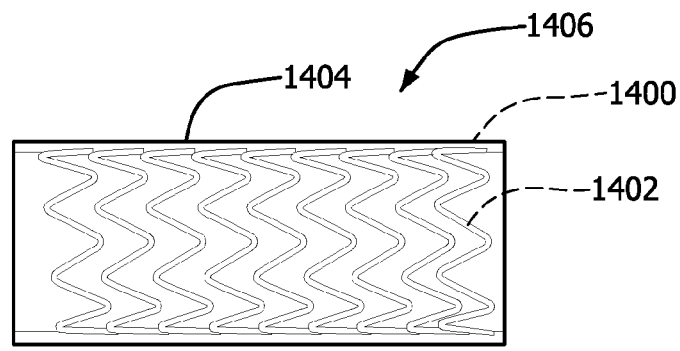
FIG. 14C is a front view of a support frame placed over a tubular substrate that is over coated with an adhesive layer.

As shown in FIG. 14C, an outer tubular member 1404 can be positioned over the substrate or graft member 1400 and the support frame 1402. The outer tubular member 1404 can have a thermoplastic or thermoset adhesive applied onto the inner surface of the outer tubular member. A thermoplastic or thermoset adhesive can also be applied onto the outer surface of the substrate or graft member 1400. A thermoplastic or thermoset adhesive can also be applied onto the outer surface of the support frame 1402.

As the term "thermoplastic" is used herein it defines a polymer that softens when exposed to heat and returns to its original condition when cooled to room temperature. Such a polymer can be made to soften, flow or take on new shapes, without significant degradation or alteration of the polymer's original condition, by the application of heat or heat and pressure.

In contrast to a thermoplastic polymer, a "thermoset" polymer is hereby defined as a polymer that solidifies or "sets" irreversibly when cured. A determination of whether a polymer is a "thermoplastic" polymer within the meaning of the present invention can be made by slowly elevating the temperature of a stressed specimen and watching for deformation. If the polymer can be made to soften, flow, or take on a new shape, without significant degradation or alteration of the polymer's original chemical condition, then the polymer is considered to be a thermoplastic. If only small amounts of material are available it may be necessary to use a hot stage microscope for this determination.

Suitable thermoplastic adhesives can include the thermoplastics previously described. A preferred thermoplastic adhesive is Fluorinated Ethylene Propylene (FEP).

The outer tubular member 1404 can be attached the substrate or graft member 1400 by heating the thermoplastic adhesive incorporated onto the outer tubular member 1404, or by heating the thermoplastic adhesive incorporated onto the substrate or graft member 1400, or by heating the thermoplastic adhesive incorporated onto the support frame 1402. By reflowing the thermoplastic adhesive, the substrate or graft member 1400 is secured to the outer tubular member 1404. The support frame 1402 is therefore laminated and secured between the substrate or graft member 1400 and the outer tubular member 1404, forming a stent graft assembly 1406 as shown in FIG. 14C.

Figure 14D:
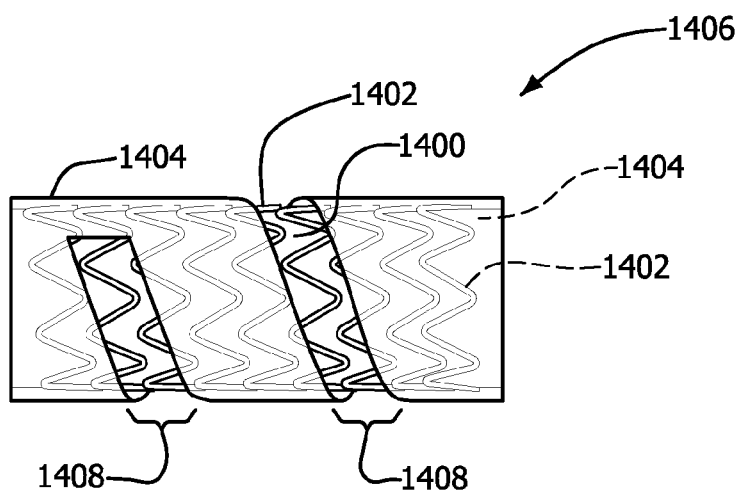
FIG. 14D is a front view of a support frame placed over a tubular substrate that is over coated with an adhesive layer, wherein portions of the over coated adhesive has been removed.

To impart a desired degree of flexibility and conformance to the stent graft assembly 1406, portions of the outer tubular member 1404 can be selectively removed 1408 as shown in FIG. 14D. Selective removal of portions of an outer tubular member 1404 can be accomplished by laser ablation, localized heating such as RF, IR, hot gas/liquids, or heated contact dies. The removed portions of the outer tubular member 1404 can have any desired shape and can form a continuous or discontinuous pattern.

Figure 15A:
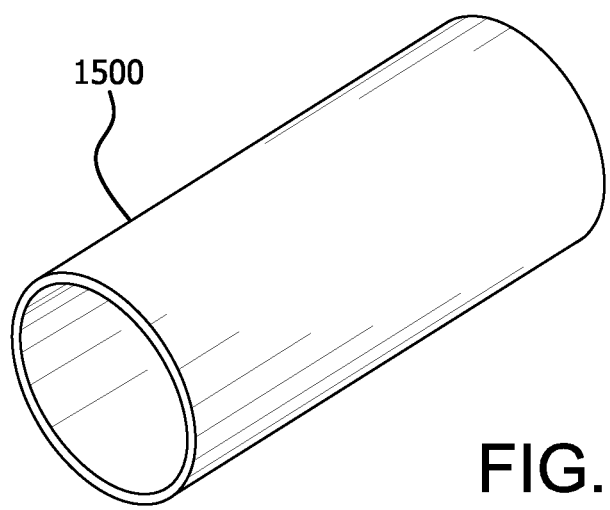
FIG. 15A is a front view of a tubular substrate.
Figure 15B:
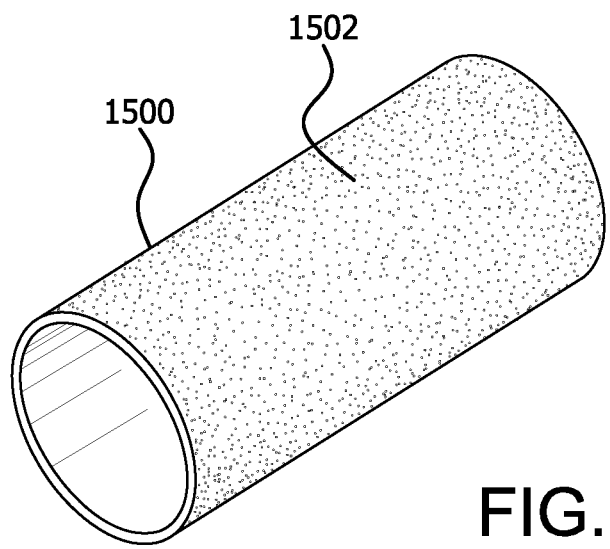
FIG. 15B is a front view of a tubular substrate over coated with an adhesive.

In an alternate process, a support frame may be attached to a substrate by use of an adhesive. After reflowing (thermoplastic) or curing (thermo-set) of the adhesive, selected portions of the adhesive can be removed to impart specific properties to the support frame/substrate. As shown in FIGS. 15A and 15B, a substrate 1500 can be coated with an adhesive

Figure 15C:
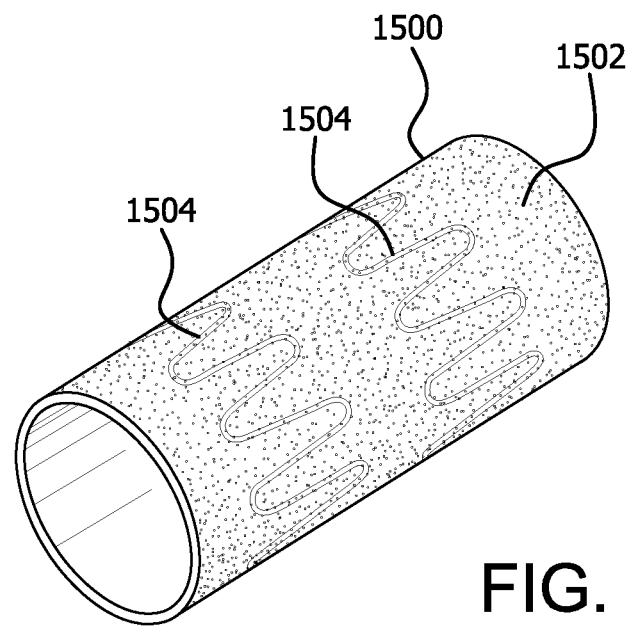
FIG. 15C is a front view of a tubular substrate over coated with an adhesive with a support frame bonded to the substrate.

1502. The adhesive 1502 can be applied using processes such as dipping, spraying, wrapping, powder coating or other processes commonly know in the art. As shown in FIG. 15C, a support frame 1504 can be positioned onto the adhesive 1502 and substrate 1500. The adhesive 1502 can then be reflowed (thermoplastic) or cured (thermo-set) to attach the support frame 1504 to the substrate 1500.

Figure 15D:
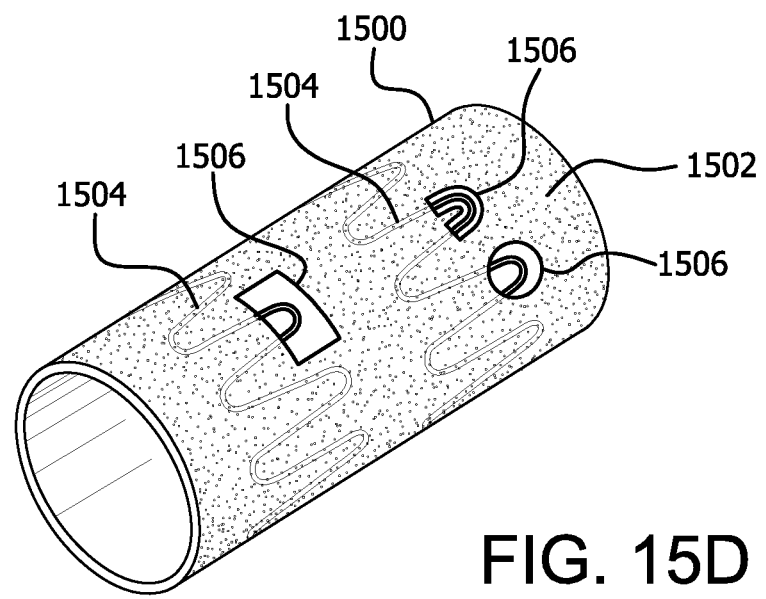
FIG. 15D is a front view of a tubular substrate over coated with an adhesive with a support frame bonded to the substrate, wherein portions of the bonding adhesive has been removed.

To impart a desired degree of flexibility and conformance to the support frame/substrate, portions of the adhesive 1502 can be selectively removed as shown in FIG. 15D. The removed portions of the adhesive 1506 can effectively "un-attach" selected portions of the support frame to the substrate. The removed portions 1506 can have any desired shape and can form a continuous or discontinuous pattern. Refer to U.S. Pat. No. 6,042,605 issued to Martin, et al., U.S. Pat. No. 6,361,637 issued to Martin, et al. and U.S. Pat. No. 6,520,986 issued to Martin, et al., describing the benefits of support frames that are not fully attached to substrates.

Portions of an adhesive can be removed by processes such as laser heating, applying hot gasses or fluids, heated contact dies, abrasive bead blasting, cutting tools and other means commonly known in the art, In an alternate process, a support frame can be pre-coated with an adhesive. An adhesive can be applied to a support frame using processes such as dipping, spraying, wrapping, powder coating or other processes commonly know in the art. Similar to the process described in FIGS. 15A through 15D, the adhesive coated wire can be positioned onto the substrate. The adhesive can then be reflowed (thermoplastic) or cured (thermo-set) to attach the support frame to the substrate. To impart a desired degree of flexibility and conformance to the support frame/substrate, portions of the adhesive can be selectively removed. The removed portions of the adhesive can effectively "un-attach" selected portions of the support frame to the substrate. The removed portions can have any desired shape and can form a continuous or discontinuous pattern.

Figure 16A:
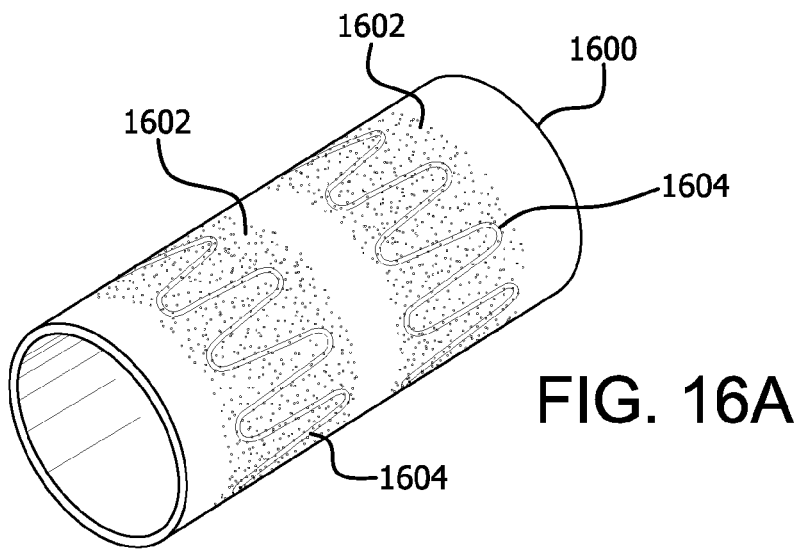
FIG. 16A is a front view of a tubular substrate partially over coated with a pattern of an adhesive with a support frame bonded to the substrate.
Figure 16B:
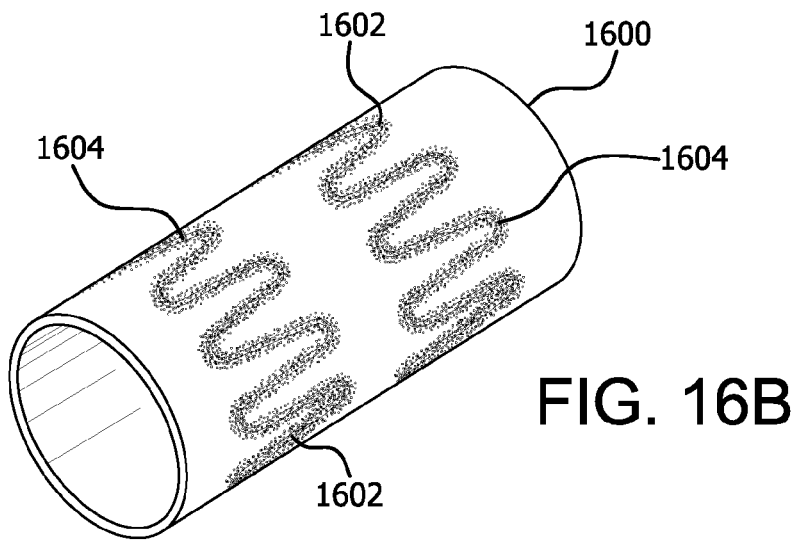
FIG. 16B is a front view of a tubular substrate partially over coated with an alternative pattern of an adhesive with a support frame bonded to the substrate.
Figure 16C:
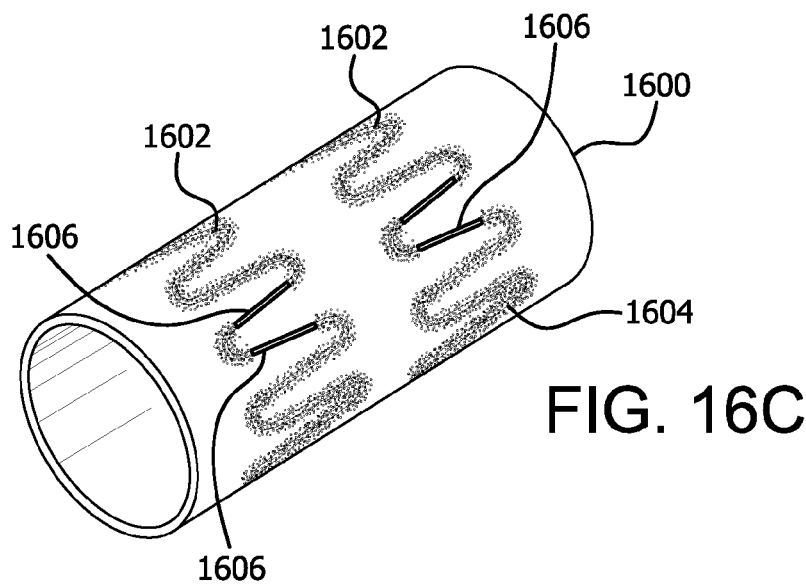
FIG. 16C is a front view of a tubular substrate over coated with a pattern of an adhesive with a support frame bonded to the substrate, wherein portions of the bonding adhesive has been removed.

In an alternate process an adhesive can be pre-coated onto a substrate only in selected areas. Shown in FIGS. 16A and 16B are an adhesive 1602 applied to a substrate 1600, forming an adhesive pattern sized to match a particular support frame pattern 1604. After placing a support frame onto the substrate and reflowing (thermoplastic) or curing (thermo-set) the adhesive, selected portions of the adhesive can be removed to impart specific properties to the support frame/substrate. Shown in FIG. 16C is a substrate 1600 where selective portions 1606 of an adhesive 1602 have been removed, effectively un-attaching portions of a support frame 1604 from the substrate 1600.

Figure 17A:
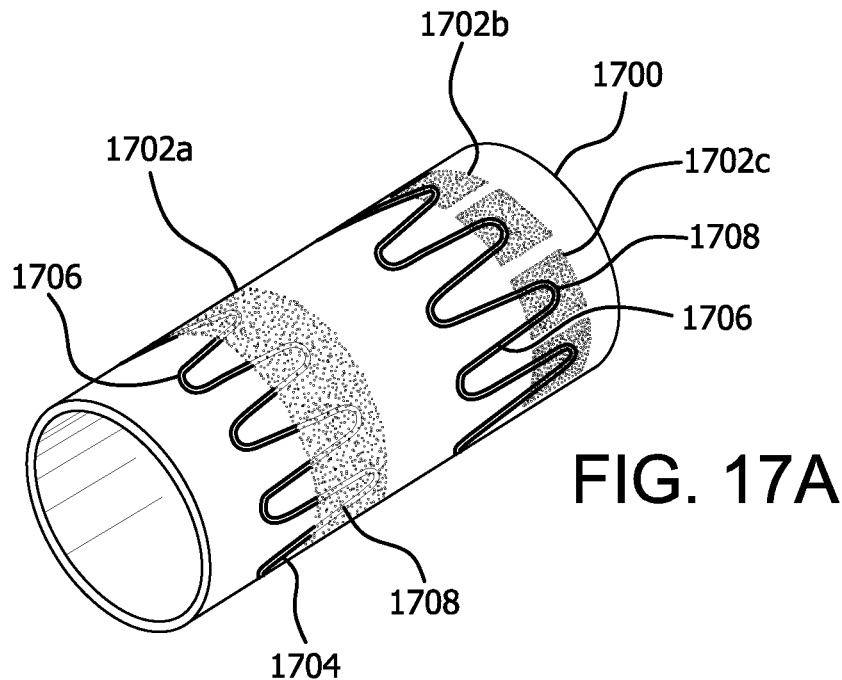
FIGS. 17A and 17B are front views of a tubular substrate over coated with a pattern of an adhesive with a support frame bonded to the substrate.

Adhesives can be applied to either a substrate and/or a support frame, forming an adhesive pattern that will not require a subsequent removal of the adhesive. Shown in FIG. 17A is a substrate 1700 having adhesive portions 1702a, 1702b and 1702c that have been pre-applied to the substrate 1700. A support frame 1704 can be positioned onto the substrate 1700 and aligned to the adhesive portions 1702a, 1702b and 1702c. The adhesive can then be reflowed (thermoplastic) or cured (thermo-set) to attach the support frame to the substrate. As shown in FIG. 17A, the support frame has portions 1708 that are attached to the substrate 1700 and portions 1706 that are not attached to the substrate 1700.

Figure 17B:
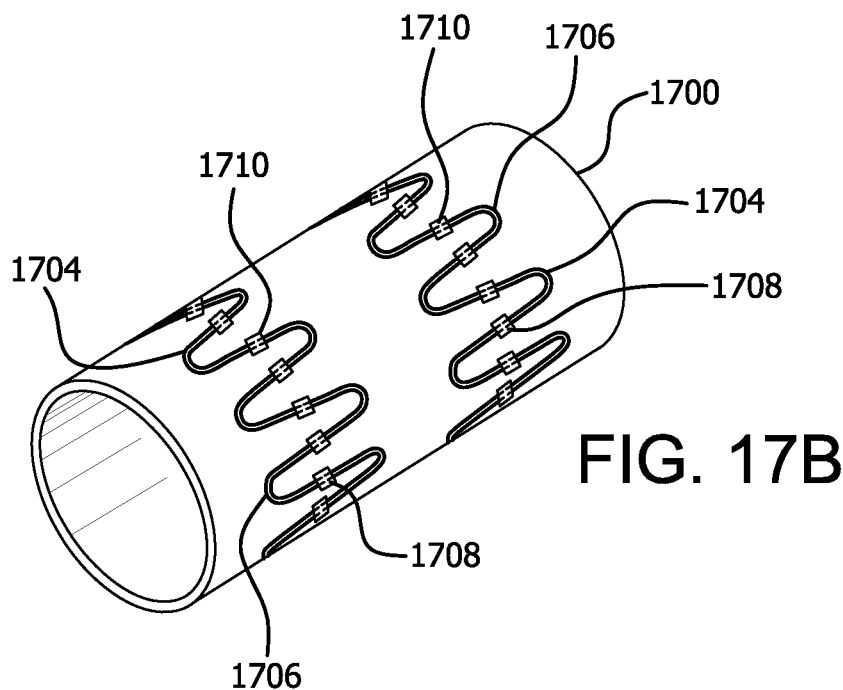

In a similar configuration, shown in FIG. 17B, a substrate 1700 can have discrete adhesive patches 1710 or areas pre applied to the substrate. A support frame 1704 can be positioned onto the substrate 1700 and aligned to the adhesive patches 1710. The adhesive can then be reflowed (thermoplastic) or cured (thermo-set) to attach the support frame to the substrate. As shown in FIG. 17B, the support frame has portions 1708 that are attached to the substrate 1700 and portions 1706 that are not attached to the substrate 1700.

Figure 18:
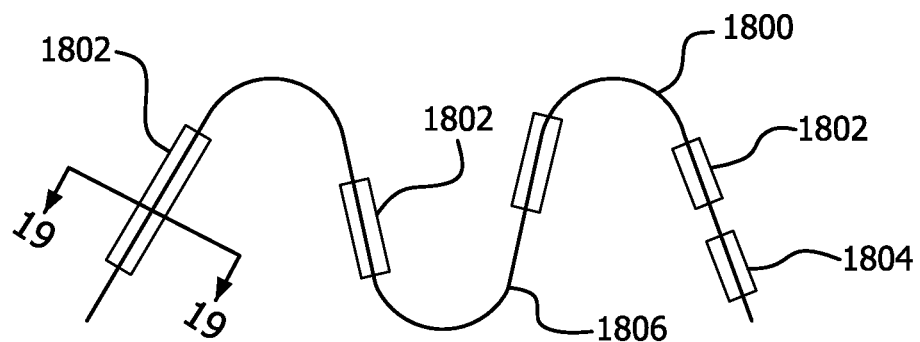
FIG. 18 is a support frame pre-coated with an adhesive pattern.
Figure 19:
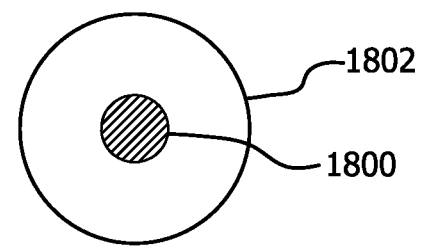
FIG. 19 is a cross-sectional view of a wire support frame pre-coated with an adhesive.

Shown in FIG. 18 and cross-sectional view FIG. 19, is a support frame 1800 having discrete portions of an adhesive 1802 pre applied to the support frame 1800. The support frame 1800 can be positioned onto a substrate. The adhesive portions 1802 can then be reflowed (thermoplastic) or cured (thermo-set) to attach the support frame to the substrate. The support frame will then have portions that are attached 1804 to the substrate 1800 and portions that are not attached 1806 to the substrate 1700.

An adhesive can be applied to a support frame along the full length of the support frame, and then in a subsequent operation, portions of the adhesive can be removed. For example a support frame can be threaded into a tubular formed adhesive and then portions of the tubular adhesive can be removed.

A thermoplastic adhesive tube can be attached to a support frame while the support frame is concurrently formed and heat treated by use of the following process:

Feed a tubular thermoplastic tube onto an un-formed length of wire. A preferred thermoplastic is FEP and a preferred wire is Nitinol.

Form the wire (and FEP tube) into a desired support frame shape.

Submerge the formed support frame (and FEP tube) into a liquid coolant bath. A suitable coolant can be chilled water, high temperature Iso-therm, high temperature Fluronert or other suitable fluids having a relatively high boiling point along with a relatively high rate of thermal conduction.

Connecting the ends of the support frame wire onto an electrical direct current source.

Passing sufficient electrical current through the support frame wire to raise the temperature of the wire and thermoplastic tube.

Continue passing sufficient electrical current through the support frame wire to raise the support frame wire temperature to a desired heat setting temperature, such as 465° C.

Remove the electrical current source from the support frame wire and allow the support frame wire to quench.

Remove the heat treated support frame and attached thermoplastic tube from the coolant bath.

The resultant support frame wire is formed and heat set to a desired shape. The thermoplastic tube reflowed and formed an attached coating onto the support frame wire. The high rate of thermal conduction, provided by the coolant bath, prevented the thermoplastic from burning while concurrently allowing the support frame wire to reach a relatively high, heat setting temperature.

Figure 20A:
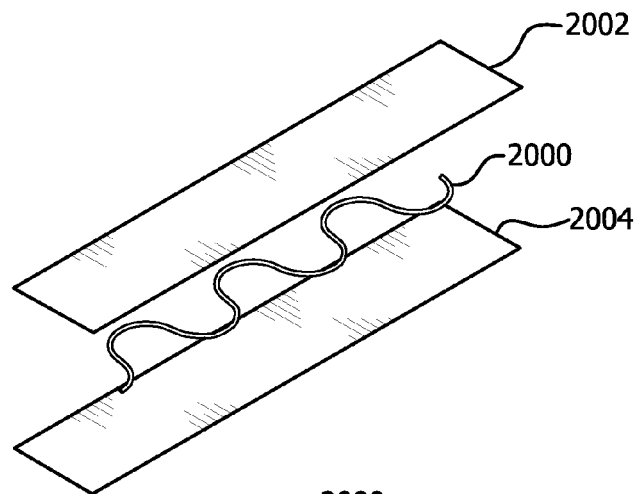
FIG. 20A is a perspective view of upper and lower layers with a support frame positioned between the layers.
Figure 20B:
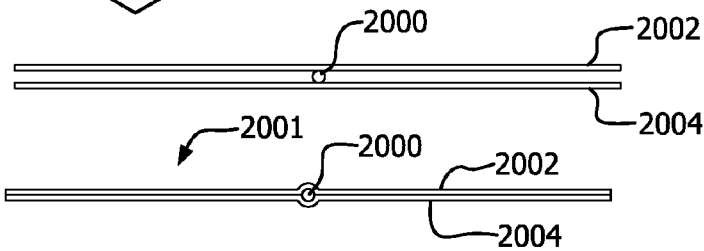
FIG. 20B is a front view of upper and lower layers with a support frame positioned between the layers.

A support frame can be laminated into a variety of materials forming a support frame with an integral web that can be subsequently used to attach to a substrate. Shown in perspective view FIG. 20A and front edge view 20B is a formed support frame 2000. The support frame can be positioned between an upper 2002 and a lower 2004 layer. The upper and lower layers can comprise polymers and other materials as previously described.

Figure 20C:
FIG. 20C is a front view of upper and lower layers with a support frame laminated between the layers.
Figure 20D:
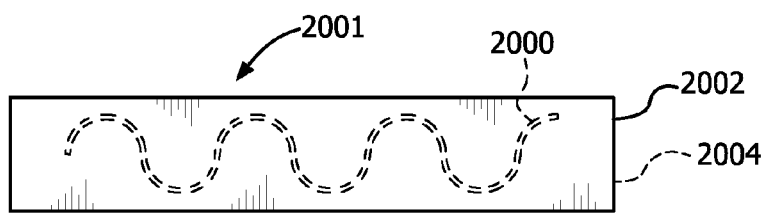
FIG. 20D is a top view of upper and lower layers with a support frame laminated between the layers.

The support frame 2000, upper layer 2002 and lower layer 2004 can be compressed to form a laminated structure 2001 as shown in edge view FIG. 20C and top view FIG. 20D.

The top layer 2002 and the bottom layer 2004 can comprise single or combinations of thermoplastics, thermo-set plastics, metals and other materials. For example the top layer 2002 and the bottom layer 2004 can comprise a thermoplastic film such as ePTFE coated with FEP. The FEP material can be reflowed to adhere the top layer 2002 to the bottom layer 2004, thereby encapsulating the support frame 2000 between the two layers. The bottom film 2004 can have an excess of the thermoplastic FEP on the bottom surface of the film to allow subsequent bonding of the laminate to a substrate.

Figure 20E:
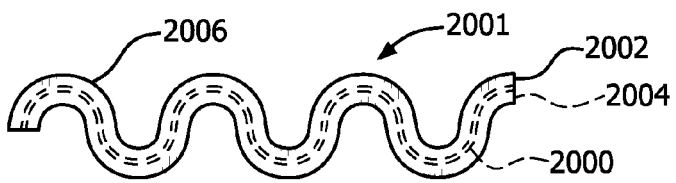
FIG. 20E is a top view of upper and lower layers, a support frame laminated between the layers, wherein the upper and lower layers have been cut to a specific pattern.
Figure 20F:
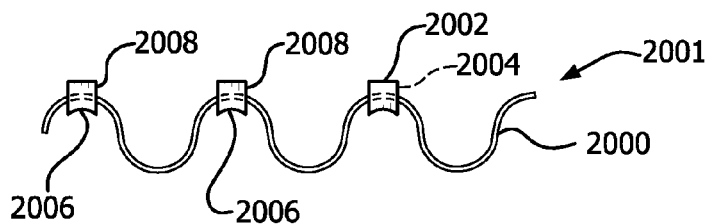
FIG. 20F is a top view of upper and lower layers, a support frame laminated between the layers, wherein the upper and lower layers have been cut to an alternate pattern.

The top layer 2002 and the bottom layer 2004 of the laminated structure 2001 can then be trimmed to form a desired pattern. As shown in FIG. 20E, the laminated structure 2001 has been trimmed to form a continuous web or bonding area 2006. The web or bonding area 2006 generally matches the shape of the formed support structure 2000. The laminated structure 2001 can alternately be trimmed to form a discontinuous pattern 2008 as shown in FIG. 20F. This trimmed laminated structure can then be wrapped or placed onto a substrate. The bonding areas 2006 can then be reflowed onto and bonded to the substrate.

A finite element analysis was performed on an undulating wire support frame attached to a substrate. The analysis focused on the derivation of mean and alternating strains induced onto the wire support frame as a result of an external loading along with a specific wire to substrate attachment "pattern". A total of 23 different wire to substrate attachment patterns were evaluated as tabulated in FIGS. 21A and 21B. As shown in FIG. 21A, a wire to substrate attachment point can be defined along a portion of an undulating wire. An attachment point at a peak (or upper) apex can be defined as position "zero"; an attachment point one half way between a peak apex and a valley apex can be defined as position "50", relating to a position that is 50% along the length between two adjacent apices; an attachment point positioned 90% along the length between two adjacent apices is defined as position "90". The 23 specific wire to substrate attachment patterns (labeled as RUN) are tabulated in FIG. 21B, defining the attachment positions and types of attachment (point or line).

Figure 22A:
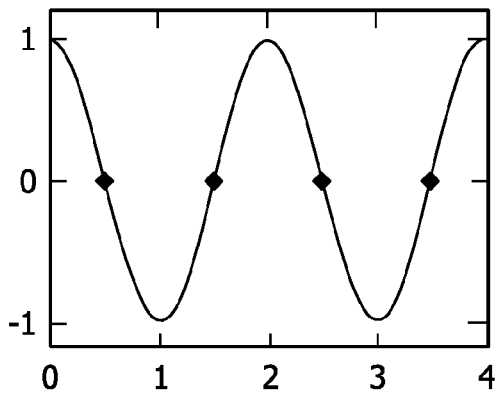
FIGS. 22A through 22W are schematics of an undulating support frames defining 23 different patterns of support frame to substrate attachment points according to the table of FIG. 21B.
Figure 22B:
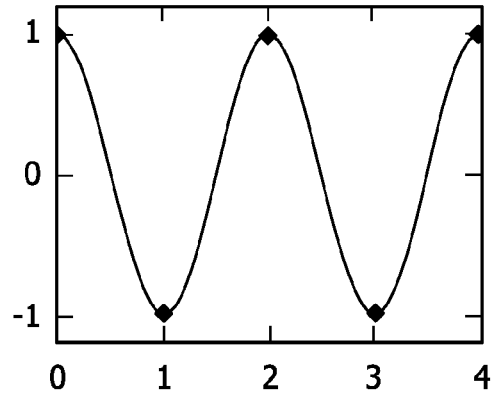
Figure 22C:
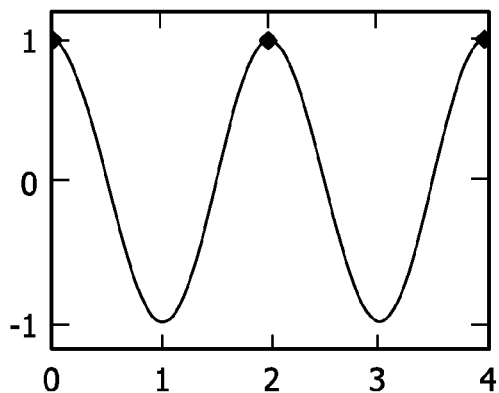
Figure 22D:
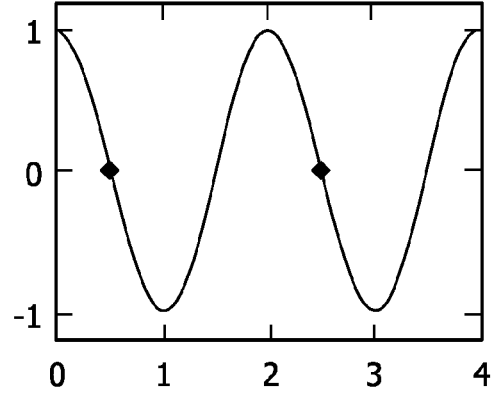
Figure 22E:
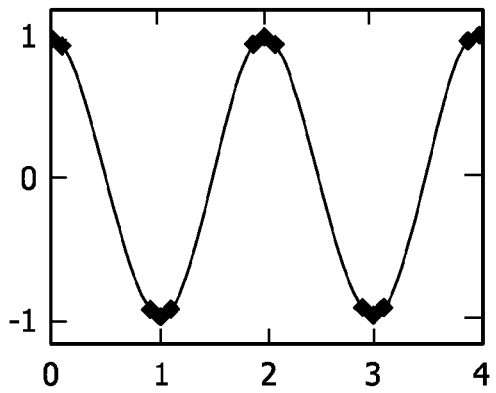
Figure 22F:
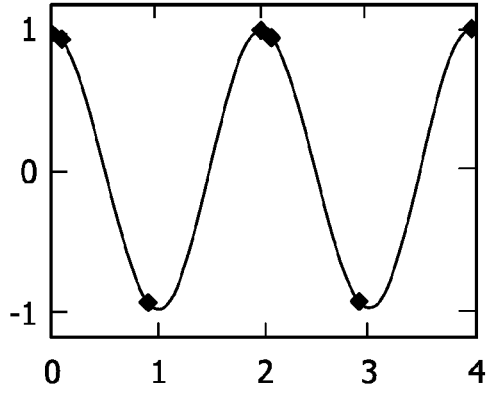
Figure 22G:
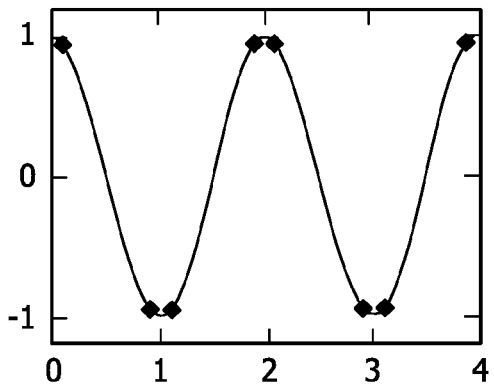
Figure 22H:
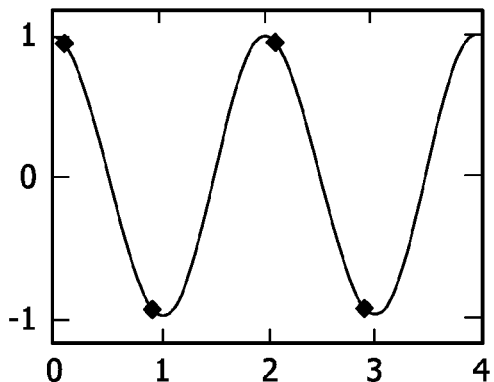
Figure 22I:
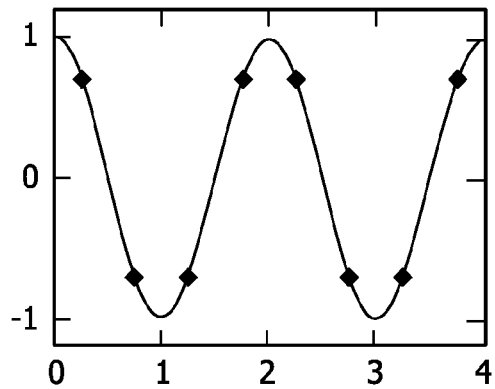
Figure 22J:
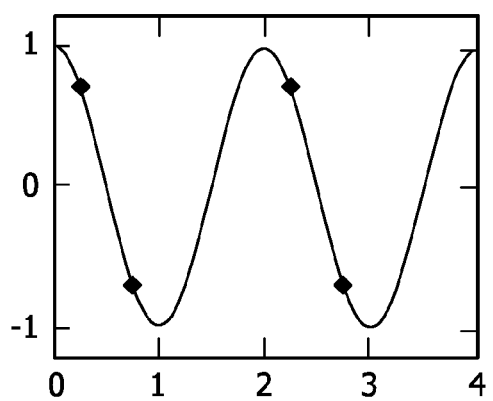
Figure 22K:
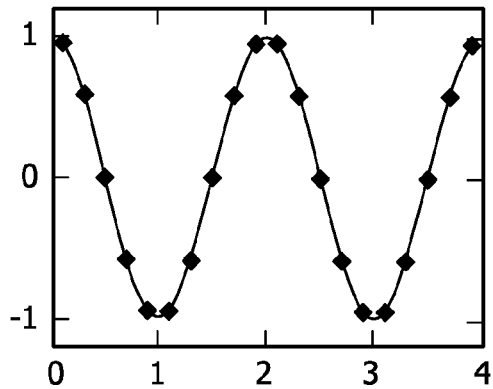
Figure 22L:
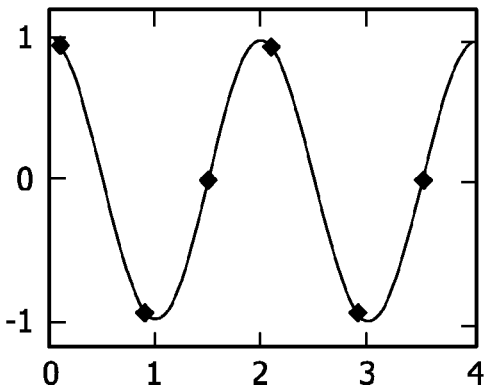
Figure 22M:
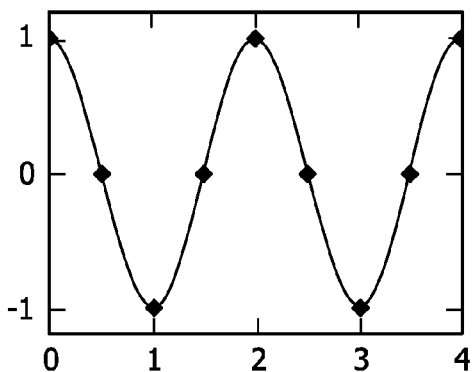
Figure 22N:
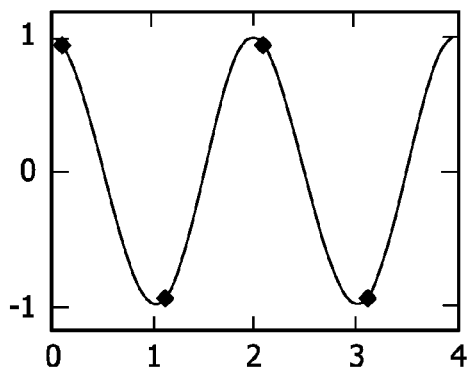
Figure 22O:
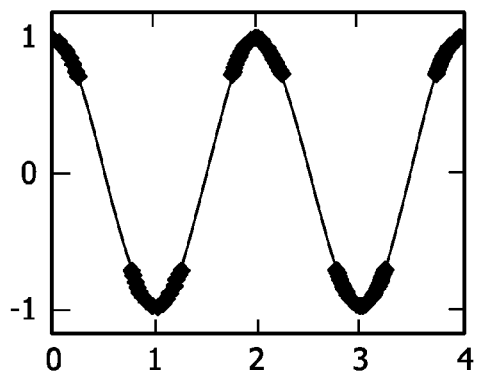
Figure 22P:
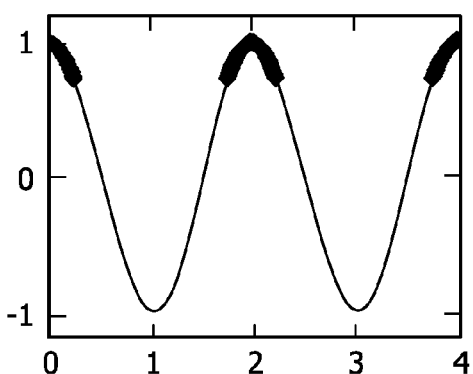
Figure 22Q:
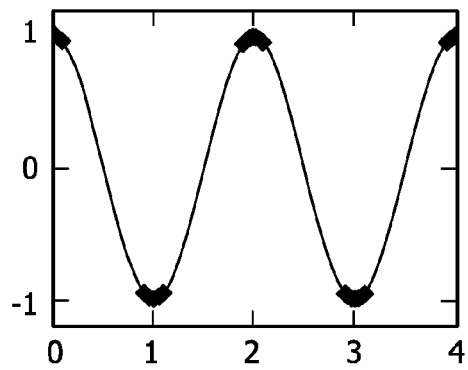
Figure 22R:
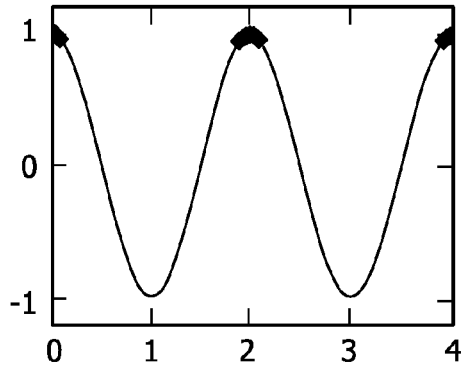
Figure 22S:
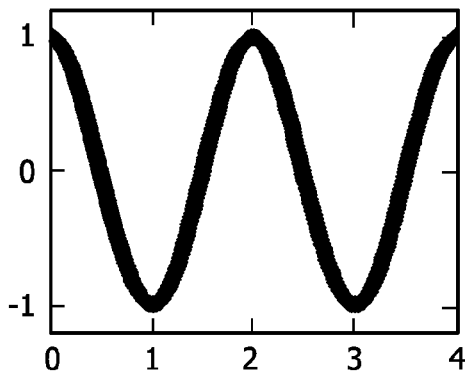
Figure 22T:
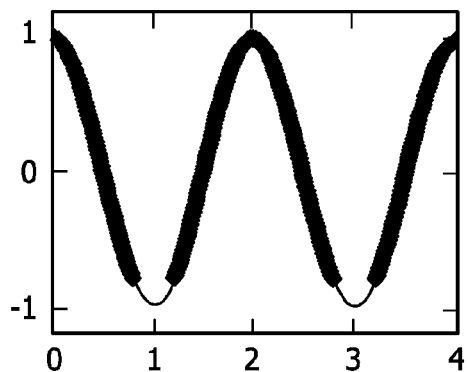

The 23 specific wire to substrate attachment patterns are depicted in FIGS. 22A through 22 W. The patterns shown match the descriptors tabulated in FIG. 21B. The finite element analysis assumed a Minimum Strain of 5% (compression) and a Maximum Strain of 25% (compression) to emulate an oversized stent graft positioned into a pulsating, elastic vessel. The mean and alternating strains (on the wire support frame) were then calculated for each of the 23 specific wire to substrate attachment patterns.

Following are details used in the finite element analysis:
I. F.E.A./3-D modeling software
  1.) Model of stent—Solidworks
  2.) Pre processing of stent—Femap
  3.) Processing of analysis—Abaqus
  4.) Post processing of analysis—C.A.E. (Abaqus)
II. Mesh properties
  1.) Stent frame element type—CD38R
  2.) Simulated PTFE element type—M3D4R
III. Material characterization
  1.) Stent frame material—Nitinol formulated from the stress-strain values, used in the input deck processed in Abaqus:
  *MATERIAL,NAME=ABQ_super_elastic_n3d
  *user material, constants=14 4.65E6, 0.35, 2.76E6, 0.35, 0.0415, 206, 77.3E3, 86.6E3 37., 1142, 43.4E3, 37.2E3, 115.95E3, 0.0415
  2.) Simulated PTFE material—A value used from hyperelastic material properties.
IV. Boundary conditions
  1.) Theta constraints on each cut surface at 180° from each other. Axial constraints at the center of each apex. (See FIG. 24)
  2.) Tied constraints were used to attach the stent frame to the simulated PTFE membrane at various designated points in this study.

Figure 24:
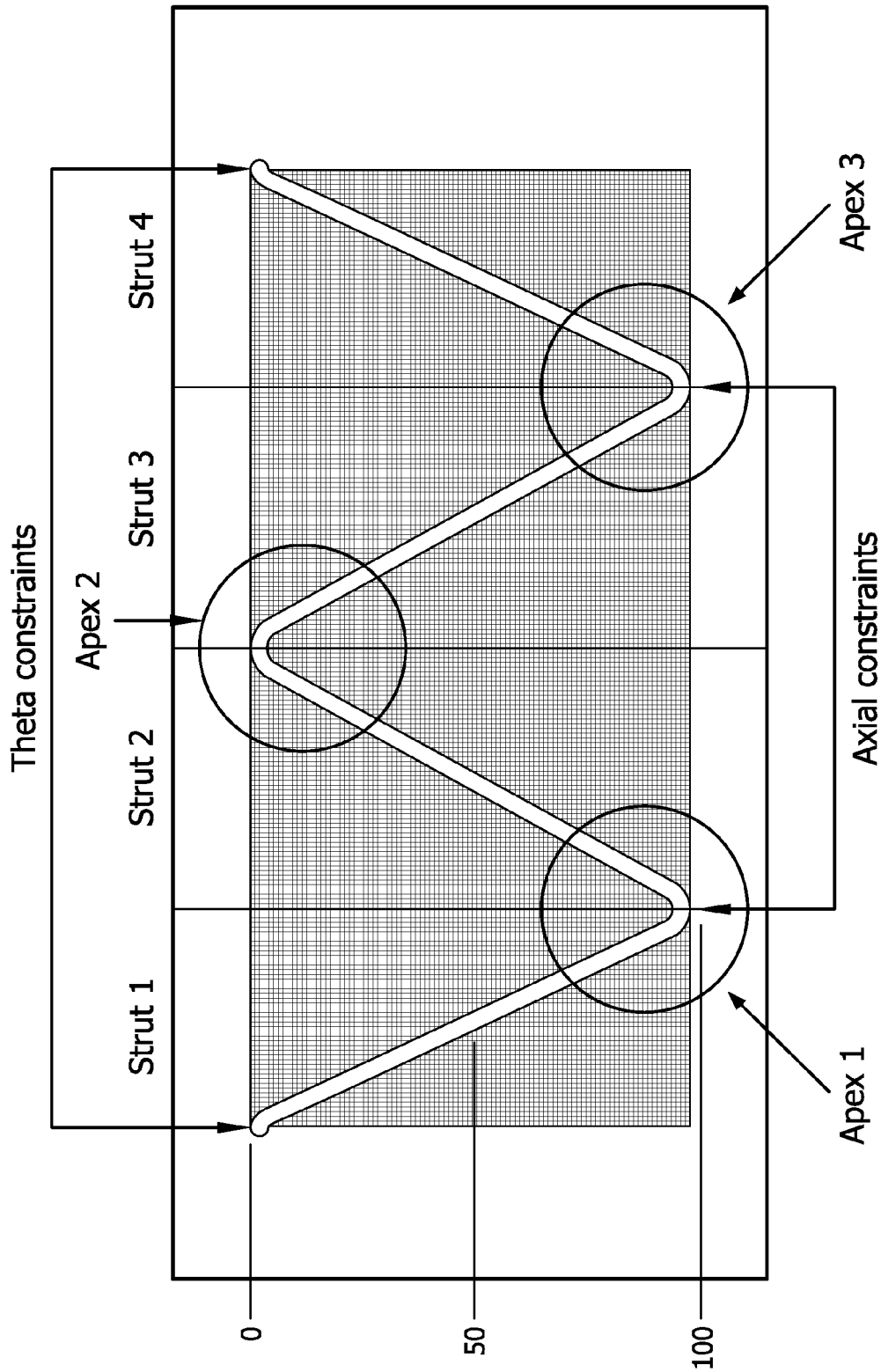
FIG. 24 is a schematic of an undulating support frame defining struts 1 through 4 and apex 1 through 3 along with theta and axial constraint locations.

V. Analysis procedure
  1.) By using an analytical rigid surface, a series of compression cycles were performed. This cycle started from 0% crush to 50% crush and then released to 25% crush. At 25% crush, all the values were reported for mean and alternating max. principal strain. The locations of the values were reported from apex 1,2 and 3 as shown in FIG. 24.

Figure 22U:
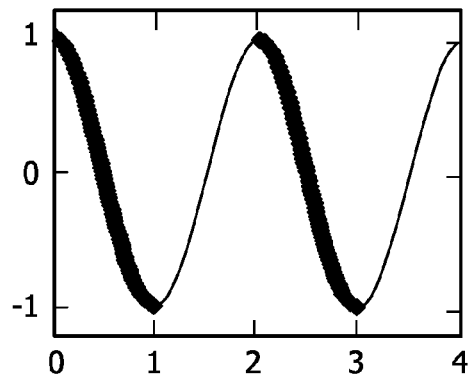
Figure 22V:
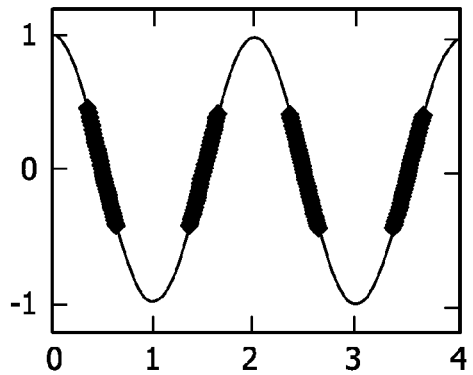
Figure 22W:
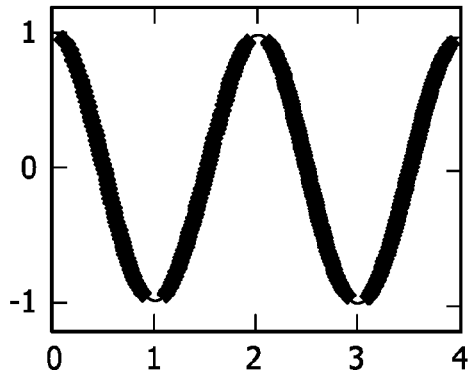
Figure 23:
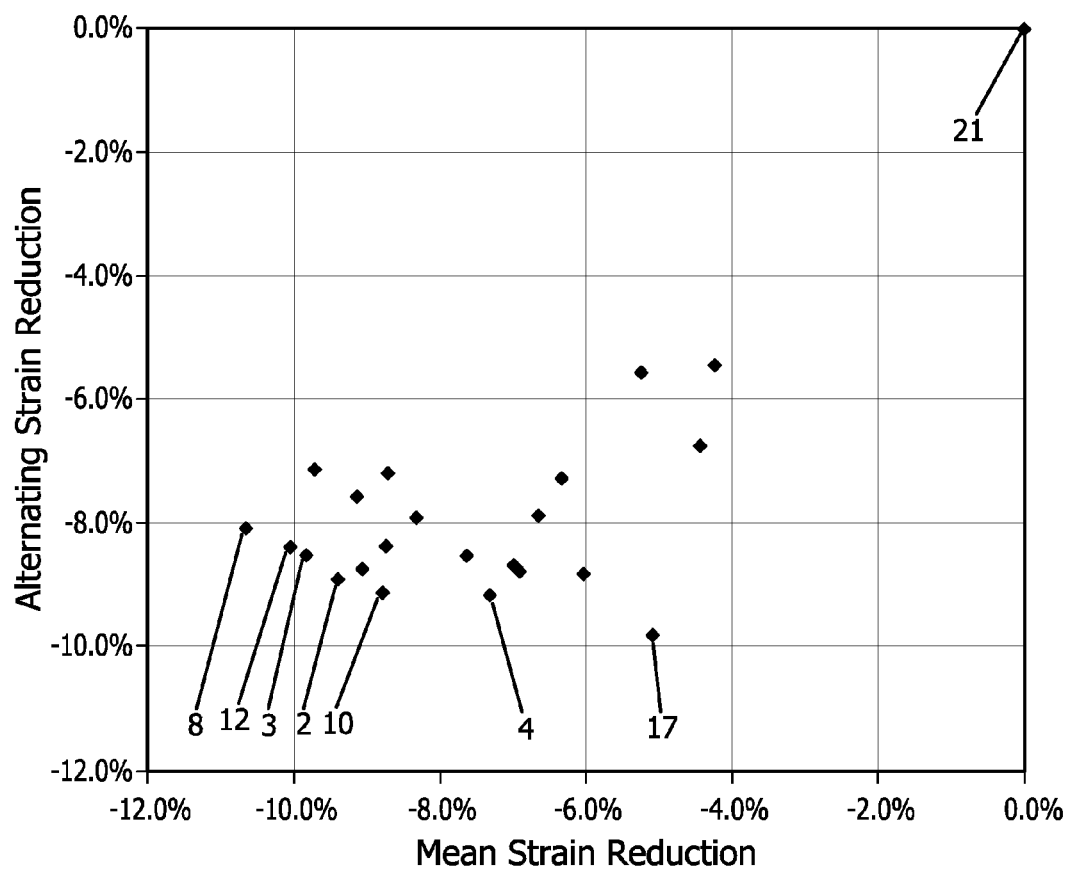
FIG. 23 is a graph plotting reductions in support frame mean and alternating strain for the patterns according to the table of FIG. 21B.

The results of the finite element analysis are summarized in FIG. 23. The highest mean and alternating strain (worst case configuration) resulted from configuration 21 (FIG. 21B and FIG. 22U). This highest mean and alternating strain data point is plotted at the upper right of FIG. 23 and is labeled as "21". The mean and alternating strains resulting from the other 22 configurations are plotted on FIG. 23 and represent a reduction (or improvement) in mean and alternating strains. As shown in FIG. 23, configurations 8, 12, 3, 2, 10, 4 and 17 (FIGS. 22 H, L, C, B, J, D and Q) all resulted in significant reductions of mean and alternating strains. Reductions in mean and alternating strains ranged from about 9% to about 11% depending on the specific attachment configuration. It is therefore apparent that support frame to substrate attachment locations can be optimized to minimize wire mean and alternating strains. Reductions in wire mean and alternating strains will improve the fatigue life of the wire in cyclical loading applications.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A method of making a medical device comprising the steps of:
   providing a first laminate material;
   positioning a support frame onto the first laminate material, the support frame having a pre-formed shape, the support frame comprising Nitinol;
   positioning a second laminate material onto the support frame and the first laminate material;
   bonding the first laminate material to the second laminate material;
   cutting the first and second laminate materials along opposite sides of the support frame thereby forming a laminated support frame having generally the same pre-formed shape of the support frame; and
   attaching the laminated support frame to a substrate.

2. The method as set forth in claim 1, wherein the first or second laminate material comprises a fluoropolymer.

3. A method of making a medical device comprising the steps of:
   providing a first laminate material;
   positioning a support frame onto the first laminate material, the support frame having a pre-formed shape, wherein the support frame is a wire;
   positioning a second laminate material onto the support frame and the first laminate material;
   bonding the first laminate material to the second laminate material;
   cutting the first and second laminate materials along opposite sides of the support frame thereby forming a laminated support frame having generally the same pre-formed shape of the support frame; and
   attaching the laminated support frame to a substrate.

4. A method of making a medical device comprising the steps of:

providing a first laminate material;
positioning a support frame onto the first laminate material, the support frame having a pre-formed shape, the support frame having an undulating shape;
positioning a second laminate material onto the support frame and the first laminate material;
bonding the first laminate material to the second laminate material;
cutting the first and second laminate materials along opposite sides of the support frame thereby forming a laminated support frame having generally the same pre-formed shape of the support frame; and
attaching the laminated support frame to a substrate.

5. The method as set forth in claim 1, wherein the first or second laminate material comprises at least two distinct fluoropolymers.

6. The method as set forth in claim 1, wherein the first and second laminate materials are bonded to the support frame.

7. The method as set forth in claim 1, wherein the attachment of the laminated support frame to the substrate defines an attachment area between the support frame and the substrate.

8. A method of making a medical device comprising the steps of:
providing a first laminate material;
positioning a support frame onto the first laminate material, the support frame having a pre-formed shape;
positioning a second laminate material onto the support frame and the first laminate material;
bonding the first laminate material to the second laminate material;
cutting the first and second laminate materials along opposite sides of the support frame thereby forming a laminated support frame having generally the same pre-formed shape of the support frame; and
attaching the laminated support frame to a substrate, the substrate being generally tubular and comprising expanded polytetrafluoroethylene.

9. The method as set forth in claim 8, wherein the support frame is nitinol.

10. The method as set forth in claim 9, wherein the support frame is generally sinusoidal.

11. The method as set forth in claim 7 wherein prior to attaching the laminated support frame to the substrate, an additional material is applied within the attachment area.

12. The method as set forth in claim 11 wherein the additional material is an adhesive.

13. The method as set forth in claim 3, wherein the first or second laminate material comprises a fluoropolymer.

14. The method as set forth in claim 3, wherein the first or second laminate material comprises at least two distinct fluoropolymers.

15. The method as set forth in claim 3, wherein the first and second laminate materials are bonded to the support frame.

16. The method as set forth in claim 3, wherein the attachment of the laminated support frame to the substrate defines an attachment area between the support frame and the substrate.

17. The method as set forth in claim 3, the support frame has an undulating shape.

18. The method as set forth in claim 3, wherein the support frame is nitinol.

19. The method as set forth in claim 4, wherein the first or second laminate material comprises a fluoropolymer.

20. The method as set forth in claim 4, wherein the support frame is nitinol.

21. The method as set forth in claim 4, wherein the support frame is a wire.

* * * * *